(12) United States Patent
Miller et al.

(10) Patent No.: US 12,378,579 B2
(45) Date of Patent: Aug. 5, 2025

(54) METHOD TO PRODUCE THE ANTI-MICROBIAL DITERPENOID LEUBETHANOL AND RELATED SERRULATANE-TYPE DITERPENES

(71) Applicant: Board of Trustees of Michigan State University, East Lansing, MI (US)

(72) Inventors: Garret P. Miller, Waltham, MA (US); Wajid Waheed Bhat, Haslett, MI (US); Emily R. Lanier, Haslett, MI (US); Sean Johnson, Bedford, MA (US); Davis T. Mathieu, East Lansing, MI (US); Björn Hamberger, Okemos, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 333 days.

(21) Appl. No.: 17/905,749

(22) PCT Filed: Mar. 5, 2021

(86) PCT No.: PCT/US2021/021156
§ 371 (c)(1),
(2) Date: Sep. 6, 2022

(87) PCT Pub. No.: WO2021/178850
PCT Pub. Date: Sep. 10, 2021

(65) Prior Publication Data
US 2023/0193328 A1 Jun. 22, 2023

Related U.S. Application Data

(60) Provisional application No. 62/986,286, filed on Mar. 6, 2020.

(51) Int. Cl.
*C12P 7/22* (2006.01)
(52) U.S. Cl.
CPC .............. *C12P 7/22* (2013.01); *C12Y 114/14* (2013.01); *C12Y 205/01087* (2013.01); *C12Y 402/03112* (2015.07)

(58) Field of Classification Search
None
See application file for complete search history.

(56) References Cited

U.S. PATENT DOCUMENTS 6,242,433 B1    6/2001   Balsamo et al.

FOREIGN PATENT DOCUMENTS

| WO | WO-2020011883 A1 | 1/2020 |
|----|------------------|--------|
| WO | WO-2021178850 A1 | 9/2021 |

OTHER PUBLICATIONS

"International Application Serial No. PCT/US2021/021156, International Search Report mailed May 25, 2021", 2 pgs.
"International Application Serial No. PCT/US2021/021156, Written Opinion mailed May 25, 2021", 6 pgs.
Gericke, et al., "Nerylneryl diphosphate is the precursor of serrulatane, viscidane and cembrane-type diterpenoids in *Eremophila* species", MC Plant Biology vol. 20(91), (Feb. 28, 2020), 1-15.
Huynh, et al., "Sesquiterpene Synthase-Catalyzed Formation of a New Medium-Sized Cyclic Terpenoid Ether from Farnesyl Diphosphate Analogues", ChemBioChem vol. 19, (2018), 1834-1838.
Johnson, Sean R., et al., "A Database-Driven Approach Identifies Additional Diterpene Synthase Activities in the Mint Family (Lamiaceae)", J. Biol. Chem, 294(4), (2019), 1349-1362.

*Primary Examiner* — Robert J Yamasaki
*Assistant Examiner* — Charles Zoltan Constantine
(74) *Attorney, Agent, or Firm* — McKee, Voorhees & Sease, PLC

(57) ABSTRACT

The disclosure relates to a method of making at least one serrulatane comprising contacting a terpene or a terpenoid substrate with at least one of a cis-prenyl transferase, a terpene synthase, and a cytochrome P45Q. The disclosure also relates to an expression system comprising one or more expression cassettes, each expression cassette comprising a promoter operably linked to a nucleic acid segment encoding at least one of: a cis-prenyl transferase, a terpene synthase, and a cytochrome P450. The disclosure also relates to a host cell comprising an expression system comprising one or more expression cassettes, each expression cassette comprising a promoter operably linked to a nucleic acid segment encoding at least one of: a cis-prenyl transferase, a terpene synthase, and a cytochrome P450.

5 Claims, No Drawings
Specification includes a Sequence Listing.

SEQUENCE LISTING

```
<160> NUMBER OF SEQ ID NOS: 6

<210> SEQ ID NO 1
<211> LENGTH: 329
<212> TYPE: PRT
<213> ORGANISM: Leucophyllum frutescens

<400> SEQUENCE: 1

Met Gln Ile Ser Leu Gln Phe Pro Lys Ala Ser Pro Cys Thr Ile Lys
1               5                   10                  15

Ser Phe Thr Thr Pro Ser Pro Pro His His Gly Asp Val Glu Thr
            20                  25                  30

Pro Cys Cys Val Ser Ser Ile Lys Ile Gly Thr Pro Trp Lys Lys Thr
            35                  40                  45

Met Val Asp His Gly Leu Ser Phe Ala Arg Phe Ser Pro Ala Ala Pro
        50                  55                  60

Leu Ser Ser Lys Phe Arg Leu Ala Ala Arg Val Glu Asp Arg Glu Ile
65                  70                  75                  80

Ser Gly Glu Ile Gln Leu Pro Asp Ala Leu Gln Ala Glu Leu Met Pro
                85                  90                  95

Lys His Val Ala Val Ile Met Asp Gly His Gly Arg Trp Ala Glu Asn
            100                 105                 110

Arg Gly Leu Pro Ile Gln His Gly His Asn Ala Gly Leu Glu Asn Leu
        115                 120                 125

Lys Gln Leu Leu Leu His Cys Cys Lys Phe Gly Ile Gly Val Leu Ser
    130                 135                 140

Val Tyr Ala Phe Ser Thr Glu Asn Trp Lys Arg Thr Lys Glu Glu Ile
145                 150                 155                 160

Asp Phe Leu Met Ser Gly Tyr Glu Cys Phe Ile Gln Tyr Val Lys
                165                 170                 175
```

```
Asp Leu Ile Leu Arg His Asp Leu Gln Phe Ser Val Ile Gly Asp Lys
            180                 185                 190

Ser Arg Leu Pro Gln Ser Ile Arg Ser Thr Ile Ala Ser Ala Glu Glu
        195                 200                 205

Ala Gly Lys Ala Asn Ser Gly Thr His Phe Val Met Ala Leu Ser Tyr
    210                 215                 220

Ser Gly Gln Tyr Asp Ile Val Asp Ala Ser Lys Lys Ile Ala Ser Gln
225                 230                 235                 240

Val Gly Ser Gly Lys Leu Arg Ala Glu Asp Ile Asp Glu Ser Val Phe
                245                 250                 255

Glu Gln Gln Leu Leu Thr Asn Val Thr Lys Phe Pro Asn Pro Asp Leu
            260                 265                 270

Leu Ile Arg Thr Ser Gly Glu Leu Arg Val Ser Asn Phe Met Leu Trp
        275                 280                 285

Gln Leu Ala Tyr Ala Glu Phe Tyr Phe Val Asp Lys Leu Phe Pro Asp
    290                 295                 300

Phe Glu Glu Ala Asp Phe Ile Glu Ala Leu Ser Ser Phe Gln Gln Arg
305                 310                 315                 320

Lys Arg Arg Tyr Gly Gly Arg Lys Lys
                325

<210> SEQ ID NO 2
<211> LENGTH: 990
<212> TYPE: DNA
<213> ORGANISM: Leucophyllum frutescens

<400> SEQUENCE: 2
atgcagatct cccttcagtt cccaaaagct tccccatgca ctatcaaaag tttcaccact    60
cctagtcctc ctcctcatca cggggacgtc gaaacaccct gctgcgtatc ttccatcaaa   120
ataggcaccc cttggaagaa acaatggtg gatcatggac tgagctttgc acgttttttct   180 ccagctgcac cttttgtcctc taagttccgt ttggcagctc gagtcgaaga ccgtgaaatt   240
agtggtgaga tccagttgcc ggacgctctg caggctgaac tgatgcctaa acacgtcgct   300
gtgatcatgg atggccacgg taggtgggcc gagaacagag ggctgccat acaacacggc   360 cacaacgcag gtctggagaa cttgaaacaa ctgcttctgc actgctgcaa atttggaatt   420
ggggttcttt cggtgtatgc cttctccacg gagaactgga gcgcactaa ggaagaaatc   480 gacttcttga tgagcggtta tgagtgtttc atacaatatt acgtgaagga tctaatactg   540
agacatgatc tgcaatttttc tgttattgga gataaatcta ggcttcctca gtctatacga   600
tctacaatag cttcggctga ggaagccggg aaggccaaca gtgggacaca ttttgtgatg   660
gcgctgagct atagcggtca atacgacata gtagatgcaa gcaagaaaat tgcaagccaa   720
gtgggaagcg ggaaactacg tgcagaagat atagatgaaa gtgtgttcga gcaacaacta   780
ttgacgaacg tcacaaagtt tccgaacccc gacttgctca tacgaacaag cggagaatta   840
agagtcagca atttcatgtt atggcaactg gcctacgcag agttctactt cgtcgacaaa   900
ctgttcccag attttgaaga ggccgacttt atagaggccc tgagttcatt ccaacagagg   960
aaaaggcgtt atggtggacg aaagaaatga                                    990

<210> SEQ ID NO 3
<211> LENGTH: 608
<212> TYPE: PRT
<213> ORGANISM: Leucophyllum frutescens
```

```
<400> SEQUENCE: 3

Met Ala Ala Pro Thr Gly Phe Ala Gln Cys Gly Thr Lys Asp Ile Phe
1               5                   10                  15

Arg Leu Pro Val Asn Val Asn Gly Arg Arg Ser Phe Leu Tyr Gly Ile
            20                  25                  30

Gln Thr Lys Ser Gln Tyr Ser Lys Tyr Gln Lys His Asn His Gly Gly
        35                  40                  45

Leu Cys Leu Arg Pro Met Ala Ala Thr Leu Asp Leu Asp Gly Gln
    50                  55                  60

Glu Asp Thr Val Ser Ser Ser Val Lys Gly His His Arg Pro Ser
65              70                  75                  80

Ser Trp Arg Thr Ile Ser Phe Ser Phe Asp Asn Gln Val Gln Glu Arg
                85                  90                  95

Tyr Ala Glu Ala Val Glu Ala Leu Lys Glu Val Arg Ala Met Val
            100                 105                 110

Met Ala Lys Asp Ser Lys Pro Arg Glu Lys Met Asn Leu Ile Asp Thr
        115                 120                 125

Leu Glu Arg Leu Gly Val Ala Tyr His Phe Lys His Glu Ile Glu Glu
    130                 135                 140

Gln Ile Glu Gln Ile Phe Lys Ser His Ala Lys Asp Asp Gly Pro Asp
145                 150                 155                 160

Ser Asp Leu Phe Thr Thr Ala Leu Tyr Phe Arg Leu Cys Arg Gln His
                165                 170                 175

Gly Tyr Asp Val Asn Ser Ser Met Phe Gly Arg Phe Lys Gly Lys Asp
            180                 185                 190

Gly Lys Phe Glu Lys Gly Leu Ile Ser Asp Ile Asn Gly Leu Leu Ser
        195                 200                 205

Leu Tyr Glu Ala Ser Tyr Leu Arg Tyr His Gly Glu Asp Ile Leu Glu
    210                 215                 220

Glu Ala Thr Val Phe Thr Thr His Tyr Leu Asn Glu Ala Lys Pro Gln
225                 230                 235                 240

Ile Leu Asp Pro Tyr Leu Arg Glu Lys Val Ala Arg Ala Leu Lys Gln
                245                 250                 255

Pro Leu His Arg Gly Val Glu Lys Leu Glu Ser Arg Tyr Tyr Ile Ser
            260                 265                 270

Val Tyr Glu Lys Tyr Glu Ser Arg Asn Glu Leu Leu Leu Lys Leu Ala
        275                 280                 285

Lys Leu Asp Phe Asn Ile Leu Gln Asn Leu Tyr Lys Lys Glu Leu Ser
    290                 295                 300

Glu Leu Phe Lys Trp Trp Lys Glu Leu Asp Leu Thr Ser Lys Leu Pro
305                 310                 315                 320

Tyr Val Arg Asp Arg Val Ala Glu Cys Phe Phe Trp Gly Met Ala Met
                325                 330                 335

Ser Tyr Glu Pro Glu Tyr Ser Leu Ser Arg Val Ala Ala Lys Ala
            340                 345                 350

Ile Val Met Ile Thr Val Leu Asn Asp Thr Tyr Glu Asn Val Ser Thr
        355                 360                 365

Leu Lys Gln Leu Glu Ile Phe Pro Glu Ile Val Gln Arg Trp Asp Thr
    370                 375                 380

Lys Asp Asn Asp Gln Leu Pro Ala Tyr Met Lys Ile Ala Tyr Glu Phe
385                 390                 395                 400

Leu Met Gly Val Tyr Glu Asp His Asp Ser Asn Val Ser Lys Gln Gly
                405                 410                 415
```

```
Arg Ser Tyr Ala Val Pro Tyr Ala Ile Glu Thr Met Ile Gln Leu Ala
            420                 425                 430

Lys Ala Tyr His Lys Ala Lys Trp Tyr Thr Gly Glu Glu Met Pro
        435                 440                 445

Thr Phe Glu Asp His Val Ser Asn Gly Ala Val Leu Ser Thr Ile Tyr
    450                 455                 460

Val Leu Leu Ser Ser Phe Tyr Ile Gly Thr Glu Ser Ala Ser Glu Glu
465                 470                 475                 480

Ala Phe Val Trp Leu Ile Asn Arg Pro Thr Ile Val Asp Ala Val Gly
                485                 490                 495

Leu Leu Gly Arg Tyr Val Asn Asp Ile Gly Thr Tyr Glu Arg Glu Cys
            500                 505                 510

Lys Gly Gly Gln Leu Ser Thr Thr Ala Ile Asp Cys Tyr Thr Arg Glu
        515                 520                 525

Asn Gly Val Ser Arg Glu Glu Thr Leu Asn Lys Phe Leu Glu Phe Ala
    530                 535                 540

Glu Asp Thr Trp Met Thr Ile Asn Lys Glu Trp Val Thr Ala Ser Cys
545                 550                 555                 560

Val Pro Arg Asp Ile Met Arg Pro Val Leu Asn Leu Gly Arg Val Gly
                565                 570                 575

Asp Thr Thr Tyr Lys Gly Gly Thr Asp Gly Tyr Thr Asp Pro Glu Ser
            580                 585                 590

Gly Leu Glu Gln Asp Ile Phe Ala Leu Phe Leu Lys Pro Ile Asp Ile
        595                 600                 605

<210> SEQ ID NO 4
<211> LENGTH: 1827
<212> TYPE: DNA
<213> ORGANISM: Leucophyllum frutescens

<400> SEQUENCE: 4
atggctgctc ccaccggctt tgctcaatgt ggtacaaaag atattttccg gctgcctgtg      60
aacgttaatg gtcgccggag ctttctatat ggtatccaaa caaaatctca gtactctaaa     120
tatcagaaac acaatcatgg aggcttgtgt ttgagaccca tggctgcagc cacccttgat     180
cttgatggtc aagaagacac cgtcagttcc agttctgtga agggtcatca tcgcccgagc     240
tcgtggagaa ctatctcatt ctcttttgac aatcaggtac aagaaagata cgcagaagct     300
gttgaagcat taaggaaga  agtaagggcc atggtgatgg ccaaagacag taaaccaaga     360
gagaaaatga atttgattga cacgcttgaa cgcttgggag tcgcttatca ctttaagcat     420
gaaattgaag agcagatcga acagatcttc aagtctcatg caaaagacga tggacctgat     480
tctgatcttt tcactactgc actctatttt cgtctgtgta caacatggg  atatgacgtc     540 aattccagta tgtttggtcg gttcaagggc aaggatggga agttcgaaaa gggtcttatt     600
agtgacatta acggtttact gagcctgtac gaagcaagtt atttgaggta tcatggggag     660
gacatcttag aagaagccac cgtcttcacg acacattact aaatgaggc  aaaaccacaa     720 atattagacc ttatcttcg  agaaaaagtg gcaagagccc taaagcaacc gcttcacagg     780
ggcgttgaga aattggagtc acgttattac atttcagtat acgagaaata tgagtcgagg     840
aatgagctgc ttctgaaact agccaaactg gatttcaaca tattgcaaaa cctgtacaaa     900
aaggagctca gtgagctgtt caagtggtgg aaggagttgg atcttacatc aaaacttcca     960
tatgtgaggg atagagtggc ggaatgcttt ttttggggca tggcgatgag ctatgaaccc    1020
```

```
gagtattcct tgtctcgagt ggctgctgcc aaggccatag taatgatcac cgttctgaat   1080
gatacgtatg aaaacgtttc aacccttaaa caactggaaa tctttcctga gattgtgcaa   1140
agatgggata ctaaagacaa tgatcagctc ccagcttata tgaagattgc ttatgaattt   1200
ctgatgggtg tatacgagga ccacgatagc aacgtgtcaa acagggaag atcttatgct    1260 gtgccctatg ccatagaaac gatgatacaa cttgcaaagg cttaccacaa gaaggcgaaa   1320
tggtacactg agaagagat gccgacattt gaagaccacg tttccaatgg ggctgtcctg    1380
agtaccatct acgtgttgct gtcgtcattt tacatcggca cagagtccgc ctccgaagaa   1440
gcgtttgttt ggctcataaa tcggcctaca attgtggatg ctgttggtct tctcggtcga   1500
tacgtgaatg atatcggcac ctacgaacgt gagtgcaagg gaggccagct ttctactacg   1560
gcaattgatt gctacacgag agagaatggt gtttcgagag aagaaactct gaataaattc   1620
cttgaatttg cggaggatac gtggatgaca atcaacaagg aatgggttac tgcaagctgt   1680
gtacccagag atattatgag gccagttctt aaccttggcc gcgtcggaga tactacctat   1740
aagggcggta cggatgggta taccgatcca gagagcggcc tcgaacaaga cattttgct    1800 ctatttctaa agccgatcga catttag                                        1827
```

<210> SEQ ID NO 5
<211> LENGTH: 599
<212> TYPE: PRT
<213> ORGANISM: Leucophyllum frutescens

<400> SEQUENCE: 5

```
Met Ala Ser Gly Ile Thr Gly Ile Gln Tyr Gly Ser Ile Glu Ile Leu
1               5                   10                  15

His Gln Pro Gly Arg Arg Asn Phe Leu Ser Asp Ile Ser Ser Ser Ile
            20                  25                  30

Gln Asn Gln Leu Lys Lys Lys Tyr Gln Tyr Glu Leu Thr Asn His Asn
        35                  40                  45

Lys Gln Leu Lys Tyr Arg Gly Leu Cys Leu Ser Arg Pro Met Ala Ala
    50                  55                  60

Ala Glu Val Leu Asp Asp Gln Glu Asp Asn Thr Thr Leu Met Thr Ser
65                  70                  75                  80

Val Lys Ala His Asp Ser Asn Phe Leu Gly Ala Ile Ser Phe Ser Phe
                85                  90                  95

Gly Asn Gln Ala Pro Phe Lys Phe Thr Thr Ser Leu Leu Ile Phe Ser
            100                 105                 110

Ser Phe Met Phe Leu Leu Val Lys Ser Ser Glu Lys Thr Lys Val Pro
        115                 120                 125

Ala Arg Lys Tyr Glu Asn Leu Pro Pro Ser Pro Lys Leu Pro Leu
    130                 135                 140

Ile Gly His Leu His His Leu Leu Gly Gly Leu Pro His His Thr Leu
145                 150                 155                 160

Ala Arg Val Thr Glu Lys Phe Gly Pro Val Val His Leu Gln Ile Gly
                165                 170                 175

Glu Ile Ser Thr Val Val Ile Ser Ser Pro Glu Ala Ala Lys Glu Val
            180                 185                 190

Leu Lys Val Arg Asp Thr Ala Cys Ala Asn Arg Pro Gln Ser Ile Ser
        195                 200                 205

Ile Glu Ile Met Leu Tyr Asn Tyr Ala Asp Phe Val Phe Ala Pro Tyr
    210                 215                 220

Asp Glu Phe Trp Arg Gln Met Arg Lys Ile Cys Ile Met Glu Met Leu
```

```
           225                 230                 235                 240
Ser Ala Arg Asn Val Lys Ser Tyr Gly Ser Ile Arg Gln Asp Glu Val
               245                 250                 255
Leu His Leu Ile Lys Ser Leu Gln Ser Ala Ser Gly Arg Ala Ile Asn
               260                 265                 270
Leu Ser Glu Lys Ile Phe Ala Thr Ser Ser Ile Val Cys Arg Val
               275                 280                 285
Ala Phe Gly Lys Val Leu Arg Asp Arg Asp Thr Leu Ile Asp Leu Met
           290                 295                 300
Lys Lys Gly Ile Ser Leu Ala Ala Gly Phe Glu Leu Val Asp Val Phe
       305                 310                 315                 320
Pro Ser Phe Lys Met Leu His Ala Val Ser Trp Asn Arg Asn Lys Leu
               325                 330                 335
Leu Lys Met His Lys Glu Leu Asp Ala Ile Leu Asp Thr Ile Val Glu
               340                 345                 350
Gly His Lys Leu Lys Glu Asn Gly Glu Tyr Gly Gly Glu Asp Ile Val
               355                 360                 365
Asp Val Leu Leu Arg Met Lys Glu Ser Gly Glu Leu Lys Phe Pro Ile
           370                 375                 380
Thr Asn Glu Asn Ile Lys Ala Val Ile Phe Asp Val Phe Ala Ala Ala
       385                 390                 395                 400
Thr Asp Thr Ser Ser Thr Val Asp Trp Ala Met Ala Glu Leu Val
               405                 410                 415
Lys Asn Pro Asn Ala Tyr Ala Lys Ala Gln Ala Glu Val Arg Gln Ala
               420                 425                 430
Phe Thr Arg Glu Glu Ile Val Asp Ala Glu Arg His Leu His Lys Leu
           435                 440                 445
Asn Tyr Leu Lys Leu Val Ile Lys Glu Thr Leu Arg Leu His Pro Pro
       450                 455                 460
Val Pro Leu Leu Pro Arg Ala Ser Arg Glu Glu Cys Glu Val Asn Gly
465                 470                 475                 480
Tyr Ser Ile Pro Leu Asn Ser Lys Val Leu Val Asn Ile Trp Ser Met
               485                 490                 495
Gly Arg Asp Pro Lys Tyr Trp Asp Glu Pro Glu Ser Phe Arg Pro Glu
               500                 505                 510
Arg Phe Glu Asn Asn Ile Glu Phe Phe Gly Asn Asn Phe Glu Tyr
           515                 520                 525
Ile Pro Phe Gly Ser Gly Lys Arg Ile Cys Pro Gly Ile Ser Phe Gly
       530                 535                 540
Met Ala Asn Val Glu Leu Pro Leu Ala His Leu Leu Tyr His Phe Asp
545                 550                 555                 560
Trp Lys Leu Pro Glu Gly Met Thr Thr Ala Asp Val Asp Leu Thr Glu
               565                 570                 575
Ala Tyr Gly Leu Ala Val Ile Arg Lys Asn Ala Leu Val Val Glu Pro
               580                 585                 590
Thr Ser Tyr Asn Pro Ser Thr
           595

<210> SEQ ID NO 6
<211> LENGTH: 1800
<212> TYPE: DNA
<213> ORGANISM: Leucophyllum frutescens

<400> SEQUENCE: 6
```

-continued

```
atggcttctg ggatcaccgg tatccaatat ggttcgatag agatcctcca tcagcccggc      60
cgccggaact ttctgagtga tatttcgtcc tctatacaga atcagcttaa gaagaagtat     120
cagtatgaac tgaccaatca taataagcaa ctcaagtaca gaggcttatg cttaagtaga     180
cccatggctg ccgccgaggt gcttgatgat caagaagaca atactactct catgacttct     240
gtcaaggctc acgactccaa cttccttggt gccatttcat tttcttttgg caatcaggca     300
cctttcaagt tcaccaccag tctcctgatt ttttcatctt tcatgttcct actggtcaag     360
tcatcggaga aaaccaaagt acccgcaaga aaatacgaaa acttgccccc aagcccacca     420
aagctgcctc tgataggcca cctccaccac ttgttgggtg ggctgccaca ccatacgcta     480
gccagagtaa ccgaaaagtt cggcccggtg gtgcatcttc agataggaga aatttctacg     540
gtggtgattt cgtcaccgga ggcagccaaa gaggtgctga aagttcgcga tactgcctgc     600
gcaaataggc ctcaaagtat cagcattgag atcatgttat acaattacgc ggactttgtc     660
tttgctcctt acgacgagtt ctggaggcag atgcgtaaga tatgcatcat ggagatgctc     720
agcgctagga atgtcaagtc ttatggatct atcaggcaag atgaggtgtt acatctcatc     780
aaatctttgc agtcagcatc tggaagagcc atcaatctga gcgagaagat atttgcgacg     840
acgagttcca ttgtgtgtag ggtggcattc gggaaggtgt tgagggatag ggacacactt     900
atagatctaa tgaaaaggg aatttccctg gcagcgggt ttgagctggt tgatgtgttt     960
ccatccttca agatgttgca cgctgtgagt tggaatagaa acaagttgtt gaagatgcac    1020
aaggagcttg acgccattct tgataccatt gttgaaggac acaagttgaa ggagaatggt    1080
gaatatggag gtgaagatat tgtagacgtt cttctcagaa tgaaggaaag tggagaactc    1140
aaatttccga ttactaacga aaacatcaaa gctgttattt ttgacgtatt cgcagctgcg    1200
acagatacct cgtctagtac cgtagattgg gccatggcag aacttgtgaa aaatcctaac    1260
gcgtacgcaa aggcacaagc tgaagtaaga caagcattta caagagagga aattgtggat    1320
gcggaacgcc acctccataa gttgaactat ctcaaacttg tgatcaaaga aactctcaga    1380
ttgcaccctc cagtcccatt actcccaga gcaagcaggg aagaatgtga agtgaatggc    1440
tattccatcc ctctcaattc taaagtgttg gtcaatattt ggtccatggg aagggatcct    1500
aaatactggg atgaacccga aagctttcga cccgagaggt ttgagaataa taacatagaa    1560
ttctttggga caactttga atacatccca ttcggatcag gaaaaaggat atgtcccggt    1620
ataagtttcg gaatggcgaa tgtggagctc ccactggctc acctcctcta tcatttcgac    1680
tggaaattac cagagggaat gacaactgct gatgtagact tgactgaggc gtatggactt    1740
gctgtcataa gaaagaatgc tcttgtcgtc gaacccacat cttacaatcc ttccacttag    1800
```

METHOD TO PRODUCE THE ANTI-MICROBIAL DITERPENOID LEUBETHANOL AND RELATED SERRULATANE-TYPE DITERPENES

CROSS-REFERENCE TO RELATED APPLICATIONS

This application is U.S. National Stage Filing under 35 U.S.C. 371 of International Patent Application Serial No. PCT/US2021/021156, filed Mar. 5, 2021, and published as WO 2021/178850 A1 on Sep. 10, 2021, which claims the benefit of priority from U.S. Provisional Appl. Ser. No. 62/986,286, filed Mar. 6, 2020, both of which are incorporated by reference as if fully set forth herein.

STATEMENT OF GOVERNMENT SUPPORT

This invention was made with government support under GM110523 awarded by the National Institutes of Health. The government has certain rights in the invention.

INCORPORATION BY REFERENCE OF SEQUENCE LISTING

A Sequence Listing is provided herewith as a text file, "2122204.txt" created on Mar. 5, 2021 and having a size of 20,480 bytes. The contents of the text file are incorporated by reference herein in their entirety.

BACKGROUND

Plant diterpenes occupy a unique molecular space with critical pharmaceutical applications over a diverse spectrum including anti-cancer, anti-microbial and immunomodulatory properties. In addition, plant-derived terpenoids have a wide range of commercial and industrial uses. Examples of uses for terpenoids include specialty fuels, agrochemicals, fragrances, nutraceuticals and pharmaceuticals. However, currently available methods for synthesis, extraction, and purification of terpenoids from the native plant sources have limited economic sustainability. Moreover, currently available methods for do not provide the substrates and methods for biosynthesis of non-natural terpenoids.

Cost-effective synthesis and access to analogs of plant diterpenoids and their derivatives is technologically limited on the levels of isolation, purification, detection, and synthesis.

SUMMARY

Described herein is a pathway for manufacturing serrulatanes that are useful as therapeutic agents. The pathway includes use of the cytochrome P450 enzyme such as CYP71D616, which can catalyze the formation of the anti-tuberculosis compound leubethanol. The biosynthetic enzymes can, for example, be from the plant *Leucophyllum frutescens*.

DESCRIPTION

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

New terpene biosynthetic methods for making new types of terpenes are described herein. Diterpenes occupy a unique molecular space with critical pharmaceutical applications over a diverse spectrum including anti-microbial, anti-cancer, immunomodulatory and psychoactive properties. Many diterpenoids are currently recognized as "drugs" (351 of over 12,500 are listed in the Dictionary of Natural Products, Taylor and Francis Group, DNP 28.1). A key challenge, however, is optimization of these compounds, and derivatization is usually not synthetically tractable.

Serrulatane diterpenoids are natural products found in plants from multiple genera within the figwort family (Scrophulariaceae). Many of these compounds have antimicrobial properties and they share a common diterpene backbone. One example, leubethanol from Texas sage, *Leucophyllum frutescens*, has demonstrated activity against multi-drug resistant tuberculosis. The structure for leubethanol (1) is shown below.

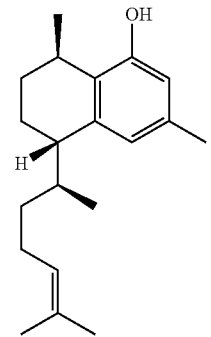

Despite potential therapeutic relevance, the biosynthesis of serrulatane diterpenoids has not been previously reported. Access to these molecules is currently limited to total chemical synthesis or extraction from natural sources.

Described herein is the full biosynthetic pathway to serrulatane diterpenoids. A short-chain cis-prenyl transferase (LfCPT1) first produces the rare diterpene precursor nerylneryl diphosphate, which is cyclized by an unusual plastidial terpene synthase (LfTPS1) into the characteristic serrulatane diterpene backbone. Final conversion to leubethanol is catalyzed by a cytochrome P450 (CYP71D616) of the CYP71 clan. This pathway documents the first case of a short-chain cis-prenyl transferase in the Lamiales order of plants and provides methods for biosynthesis of diverse diterpenoids in *Eremophila*. LfTPS1 represents an example of neofunctionalization and acceptance of a novel substrate after localization to the plastid. Biosynthetic access to the serrulatane backbone and leubethanol provides a pathway for manufacture of complex serrulatane diterpenoids, a diverse class of promising antimicrobial therapeutics.

Examples of serrulatanes that can be synthesized using the methods described herein include compounds of the general formula:

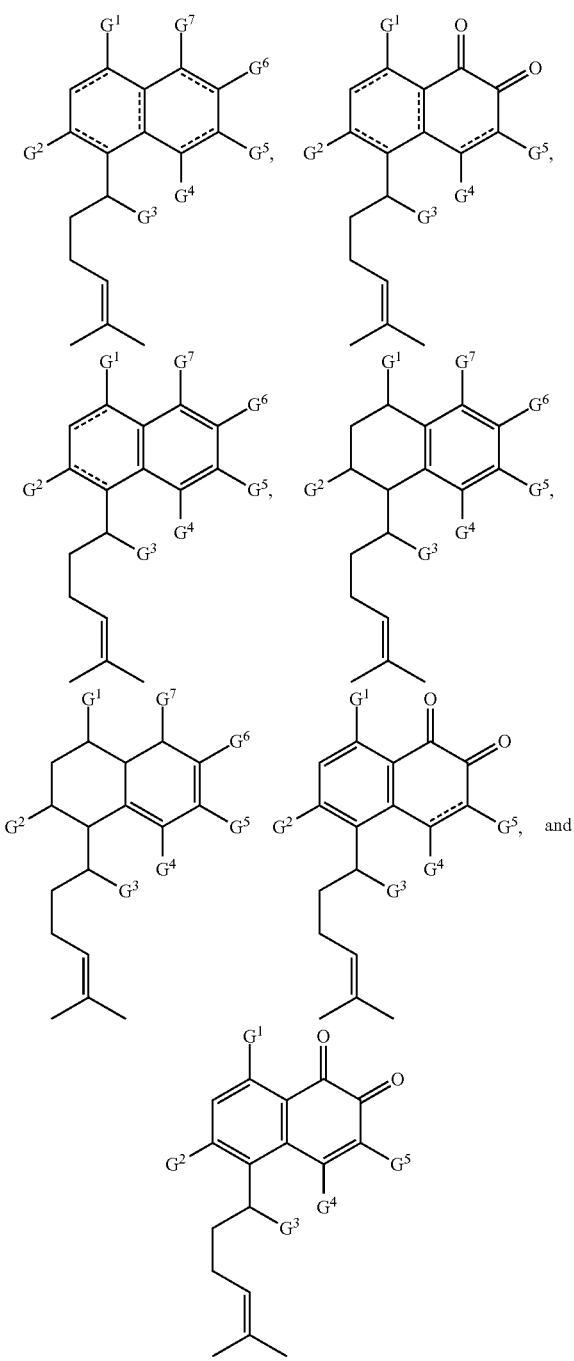

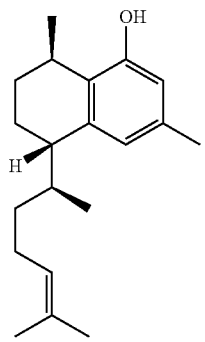

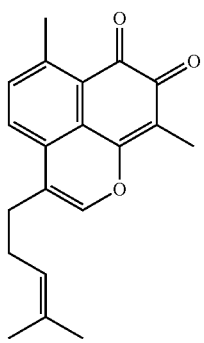

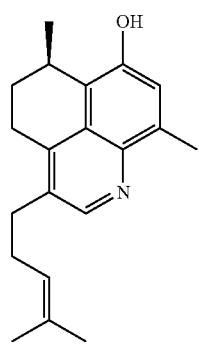

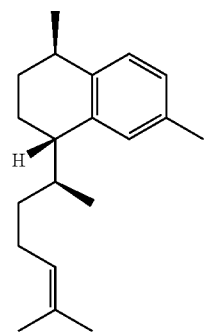

wherein:
- G¹ is substituted or unsubstituted alkyl (e.g., $(C_1-C_5)$-alkyl, such as methyl);
- G² is H, substituted or unsubstituted alkyl (e.g., $(C_1-C_5)$-alkyl, such as methyl), or OG⁸, wherein G⁸ is H, substituted or unsubstituted alkyl (e.g., $(C_1-C_5)$-alkyl), or acyl (e.g., $(C_1-C_5)$-alkyl-C(O)—, such as acetyl);
- G³ is substituted or unsubstituted alkyl (e.g., $(C_1-C_5)$-alkyl, such as methyl);
- G⁴ is H, substituted or unsubstituted alkyl (e.g., $(C_1-C_5)$-alkyl), or G⁴ and G³, together with the atoms to which they are attached, can form a five- or six-membered heterocyclyl;
- G⁵ is substituted or unsubstituted alkyl (e.g., $(C_1-C_5)$-alkyl, such as methyl) or C(O)OG⁸ (e.g., $CO_2H$ and esters); and
- G⁶ and G⁷ are each, independently, H or OG⁸ (e.g., where G⁸ is $(C_1-C_5)$-alkyl-C(O)—, such as acetyl), such as the following compounds:

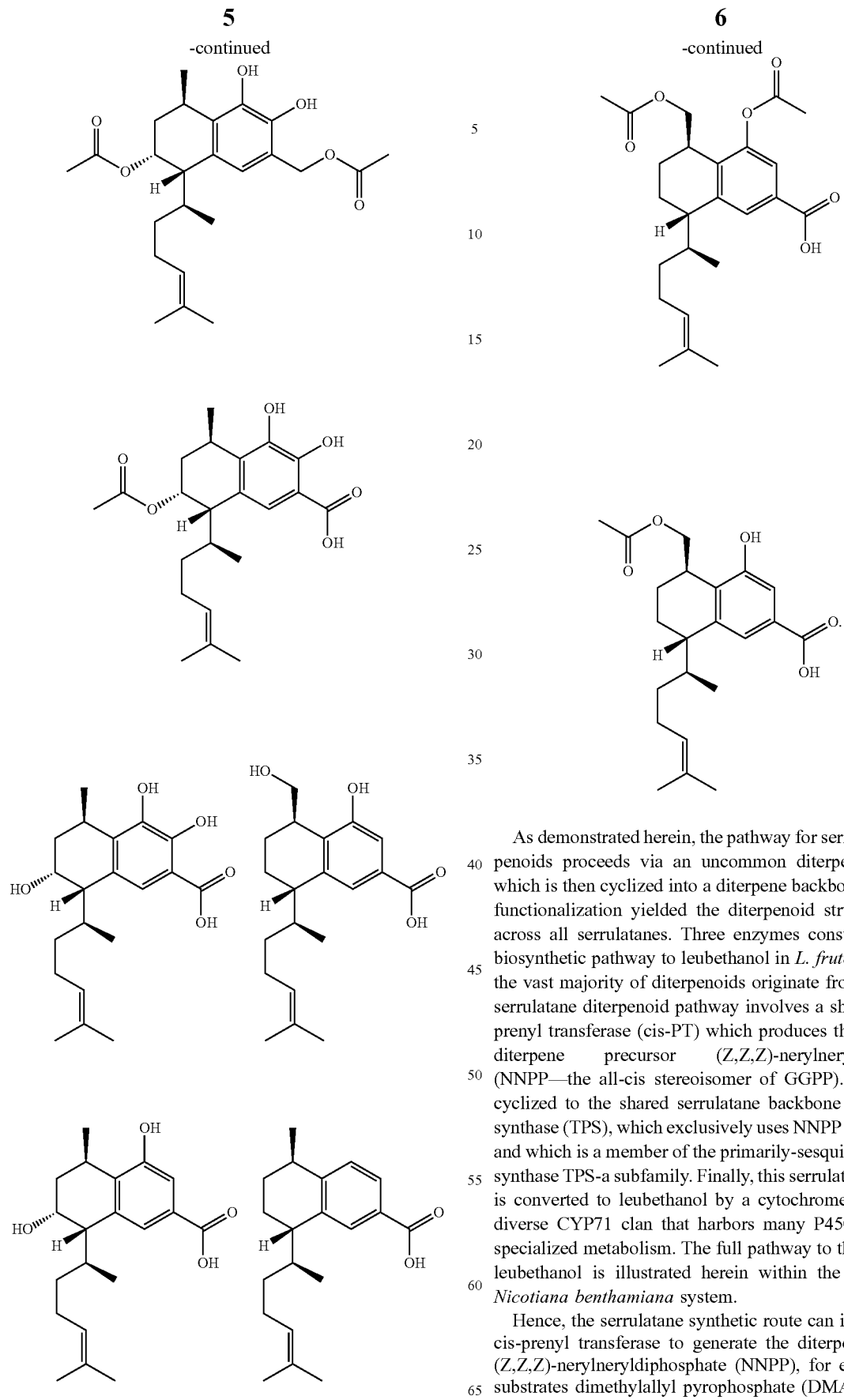

As demonstrated herein, the pathway for serrulatane diterpenoids proceeds via an uncommon diterpene precursor which is then cyclized into a diterpene backbone. Oxidative functionalization yielded the diterpenoid structure shared across all serrulatanes. Three enzymes constitute the full biosynthetic pathway to leubethanol in *L. frutescens*. While the vast majority of diterpenoids originate from GGPP, the serrulatane diterpenoid pathway involves a short-chain cis-prenyl transferase (cis-PT) which produces the uncommon diterpene precursor (Z,Z,Z)-nerylneryidiphosphate (NNPP—the all-cis stereoisomer of GGPP). This is then cyclized to the shared serrulatane backbone by a terpene synthase (TPS), which exclusively uses NNPP as a substrate, and which is a member of the primarily-sesquiterpene (C15) synthase TPS-a subfamily. Finally, this serrulatane backbone is converted to leubethanol by a cytochrome P450 of the diverse CYP71 clan that harbors many P450s of terpene specialized metabolism. The full pathway to the serrulatane leubethanol is illustrated herein within the heterologous *Nicotiana benthamiana* system.

Hence, the serrulatane synthetic route can involve use of cis-prenyl transferase to generate the diterpene precursor (Z,Z,Z)-nerylneryldiphosphate (NNPP), for example from substrates dimethylallyl pyrophosphate (DMAPP) and isopentenyl pyrophosphate (IPP). The structure of (Z,Z,Z)-nerylneryldiphosphate (NNPP) is shown below.

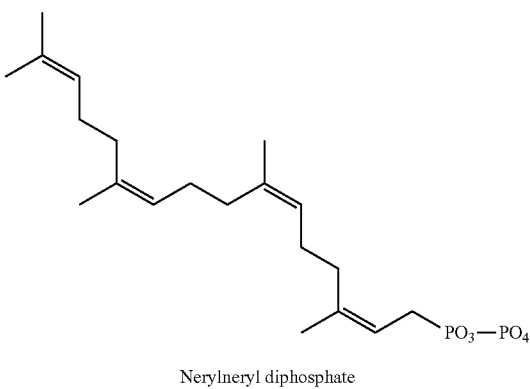

Nerylneryl diphosphate

An example of a sequence for a cis-prenyl transferase from *Leucophyllum frutescens* (LfCPT1) that can synthesize this reaction is provided as SEQ ID NO:1.

A nucleotide sequence for the *Leucophyllum frutescens* LfCPT1 with SEQ ID NO: 1 is provided as SEQ ID NO:2.

The (Z,Z,Z)-nerylneryldiphosphate (NNPP) is then cyclized to the shared serrulatane backbone by a terpene synthase (TPS) to provide the following compound.

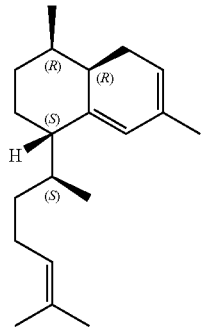

Compounds such as the compound of formula 1 can then be accessed as follows:

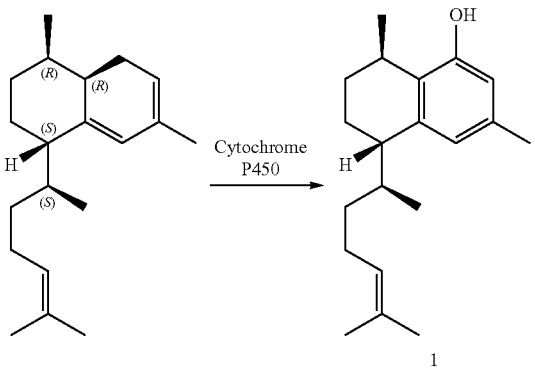

b An example of a sequence for a terpene synthase from *Leucophyllum frutescens* (LfTPS1) that can synthesize this cyclization reaction is provided as SEQ ID NO:3.

A nucleotide sequence for the *Leucophyllum frutescens* LfTPS1 with SEQ ID NO:3 is provided as SEQ ID NO:4.

An example of a sequence of a cytochrome P450 (CYP71D616) enzyme that can convert this cyclized serrulatane backbone to leubethanol is provided as SEQ ID NO:5.

A nucleotide sequence for the *Leucophyllum frutescens* CYP71D616 with SEQ ID NO:5 is provided as SEQ ID NO:6.

Therefore, described herein is a chemical strategy to synthesize diterpene class.

Enzymatic biosynthesis of pharmaceutically active compounds is increasingly important for securing access to relevant chemistries, scalability of production, and long-term reduction in cost for synthesis of serrulatanes. Genetic information was used to reconstruct the pathways to serrulatanes, especially the pharmacologically active serrulatanes.

The enzymes described herein can have some sequence variations. For example, enzymes described herein can have one or more deletions, insertions, replacements, or substitutions in a part of the enzyme. The enzyme(s) described herein can have, for example, at least 60%, or at least 70%, or at least 80%, or at least 90%, or at least 93%, or at least 95%, or at least 96%, or at least 97%, or at least 98%, or at least 99% sequence identity to a sequence described herein.

In some cases, enzymes can have conservative changes such as one or more deletions, insertions, replacements, or substitutions that have no significant effect on the activities of the enzymes. Examples of conservative substitutions are provided below in Table 1A.

TABLE 1A

| Conservative Substitutions | |
|---|---|
| Type of Amino Acid | Substitutable Amino Acids |
| Hydrophilic | Ala, Pro, Gly, Glu, Asp, Gln, Asn, Ser, Thr |
| Sulfhydryl | Cys |
| Aliphatic | Val, Ile, Leu, Met |
| Basic | Lys, Arg, His |
| Aromatic | Phe, Tyr, Trp |

A variety of additional enzymes can be used in the methods described herein. For example, the methods can also include use of one or more transcription factor, cis-prenyl transferase, terpene synthase, cytochrome P450, cytochrome P450 reductase, 1-deoxy-D-xylulose 5-phosphate synthase (DXS), 1-deoxy-D-xylulose 5-phosphate-reducto-isomerase, cytidine 5'-diphosphate-methylerythritol (CDP-ME) synthetase (IspD), 2-C-methyl-d-erythritol 2,4-cyclodiphosphate synthase (IspF), geranylgeranyl diphosphate synthase (GGDPS), HMG-COA synthase, HMG-CoA reductase (HMGR), mevalonic acid kinase (MVK), phosphomevalonate kinase (PMK), mevalonate-5-diphosphate decarboxylase (MPD), isopentenyl diphosphate isomerase (IDI), abietadiene synthase (ABS), farnesylpyrophosphate synthase (FPPS), ribulose bisphosphate carboxylase, squalene synthase (SQS), patchoulol synthase, or WRI1 protein.

Such enzymes can be obtained from organisms such as *Leucophyllum frutescens* (Lf), *Tripterygium wilfordii* (Tw), *Euphorbia peplus* (Ep), *Coleus forskohlii* (Cf), *Ajuga reptans* (Ar), *Perovskia atriciplifolia* (Pa), *Nepeta* mussini (Nm), *Origanum majorana* (Om), *Hyptis suaveolens* (Hs), *Grindelia robusta* (Gr), *Leonotis leonurus* (Ll), *Marrubium vulgare* (Mv). *Vitex agnus-castus* (Vac), *Euphorbia peplus* (Ep), *Ricinus communis* (Rc), *Daphne genkwa* (Dg), *Zea mays* (Zm), and other organisms. U.S. Provisional Application Ser. No. 62/930,898, filed Nov. 5, 2019 provides further information on these enzymes. U.S. Provisional Application Ser. No. 62/930,898, filed Nov. 5, 2019, is incorporated herein by reference in its entirety.

Substrates

The methods described herein can include use of different substrates to produce a variety of different products.

Taking advantage of natural substrate promiscuity, precursor-directed biosynthesis was used to generate variants of the drugs in the family of non-ribosomal peptides, polyketides and non-natural indole alkaloids. Modification of natural products can provide analogs with improved or novel medicinal properties. To that end, the disclosure relates to substrates of the formula (I), (Ia) or (II):

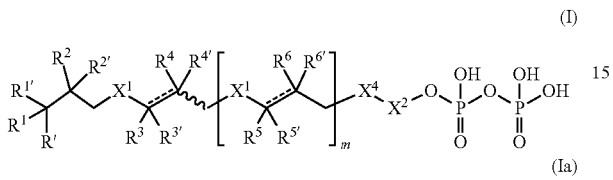
(I)

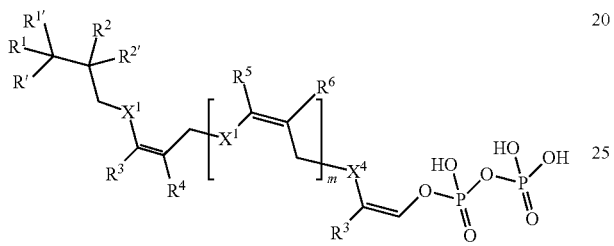
(Ia)

-continued

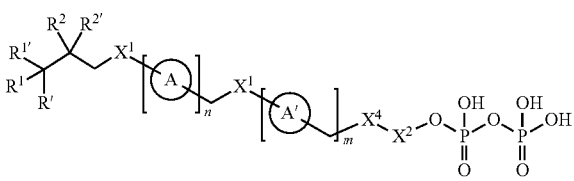
(II)

wherein:
  m is an integer from 0 to 3 (e.g., 1 or 2), with the understanding that if m is 2 or 3,
  each repeating subunit can be the same or different;
  n is an integer from 0 to 1;
  the dashed lines (------) represent a double bond when $R^{3'}$ and $R^{4'}$ are absent or when $R^{5'}$ and $R^{6'}$ are absent,
  A and A' are each independently cycloalkyl, aryl or heterocyclyl, each of which can be optionally substituted;

$X^1$ is a heteroatom, —$X^3$-alkyl, -alkyl-$X^3$— or alkyl, wherein $X^3$ is a heteroatom or alkyl or $X^1$ is:

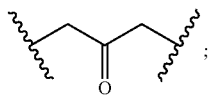 [SMILES: *CC(=O)C*]

$R^1$ and $R^2$ form a double bond or an epoxide;
each R', $R^{1'}$, $R^2$, $R^{2'}$ and $R^3$-$R^6$ is, independently, H, alkyl, halo, aryl, and alkylaryl;
$R^{3'}$ and $R^{4'}$ are absent or $R^{5'}$ and $R^{6'}$, together with the carbon atoms to which they are attached, form an epoxide, a cycloalkyl group, an aryl group or a heterocyclyl group;
$R^{5'}$ and $R^{6'}$ are absent or $R^{5'}$ and $R^{6'}$, together with the carbon atoms to which they are attached, form an epoxide, a cycloalkyl group, an aryl group or a heterocyclyl group;
$X^2$ is a bond, alkenyl or acyl; and
$X^4$ is a absent, a heteroatom or alkyl;
with the proviso that the compound of the formula (I) is not a compound of the formula:

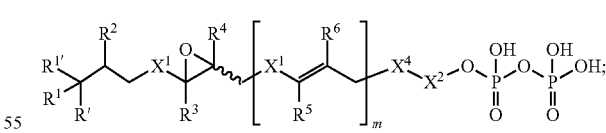

Examples of compounds of the formula (I) include compounds of the formula:

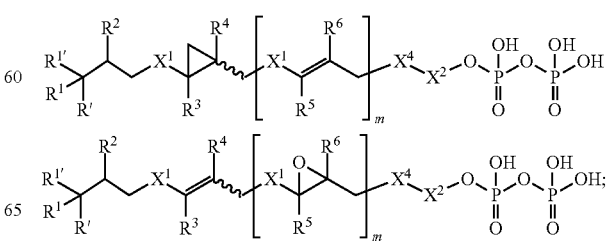

-continued

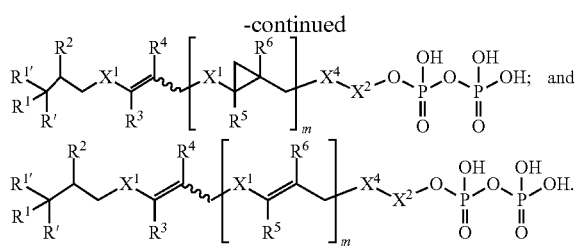

Examples of the formula (II) include compounds of the formula:

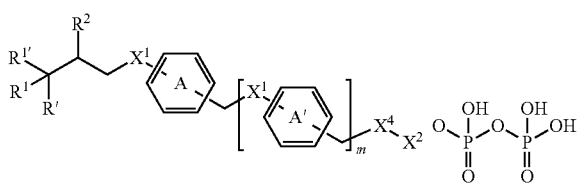

Examples of compounds of the formula (I) include compounds wherein if $X^1$ is a heteroatom, the heteroatom is oxygen. Other examples of compounds of the formula (I) include compounds wherein $X^3$ is oxygen or $C_1$-$C_5$-alkyl, such as —$CH_2$— and $C_2$-$C_3$-alkyl. Still other examples of compounds of the formula (I) include compounds wherein $R^3$-$R^6$ are each H or $C_1$-$C_5$-alkyl, such as methyl and $C_2$-$C_3$-alkyl. Still other examples of compounds of the formula (I) include compounds wherein $R^3$ and $R^5$ are each H or $C_1$-$C_5$-alkyl, such as methyl and $C_2$-$C_3$-alkyl; and $R^4$ and $R^6$ are each H. Yet other examples of compounds of the formula (I) include compounds wherein m is 1 or 2. In other examples, m is 0. Other examples of compound of the formula (I) include compounds wherein $X^2$ is an alkenyl group of the formula:

or an acyl group of the formula:

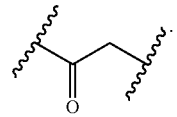 [SMILES: *CC(*)=O]

Examples of compounds of the formula (I) include compounds of the formulae;

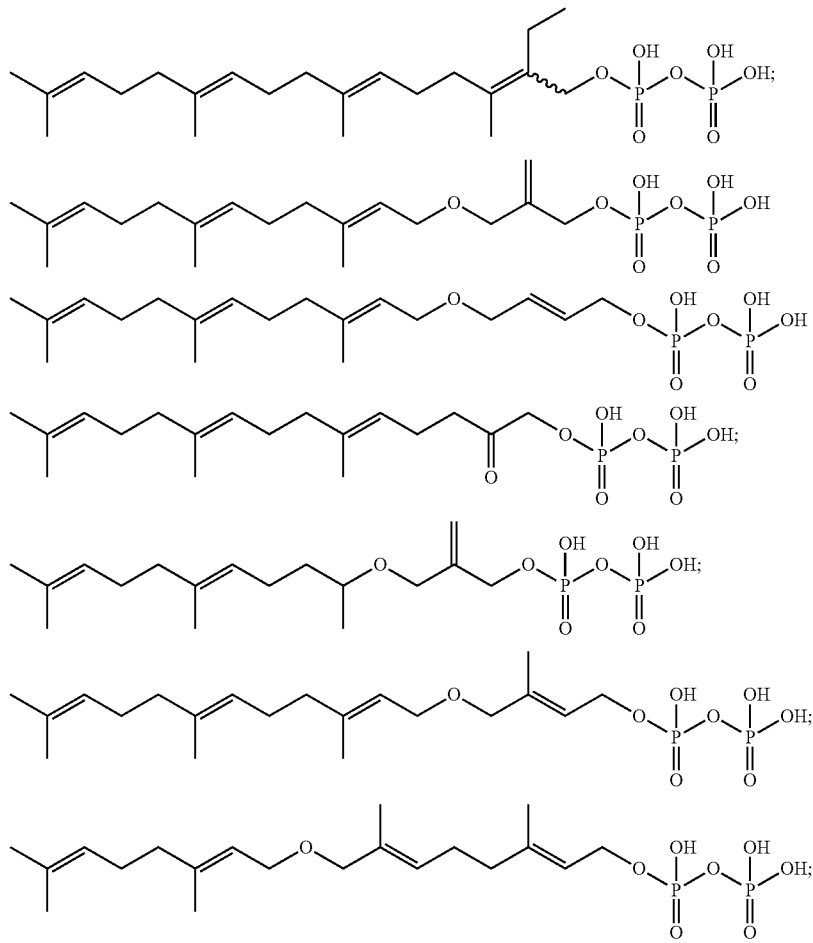

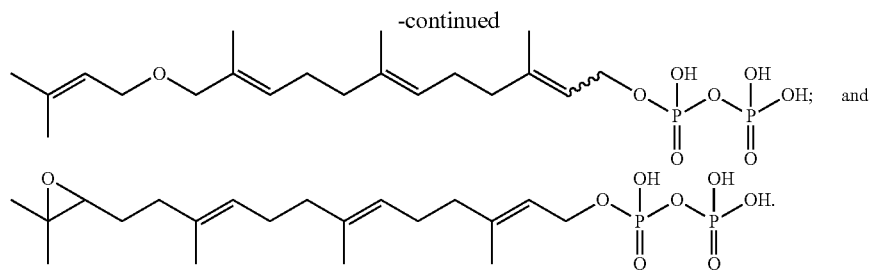

The compounds of the formula (I) or (II) can be enzymatically transformed into terpenoids having compound cores of the formula:

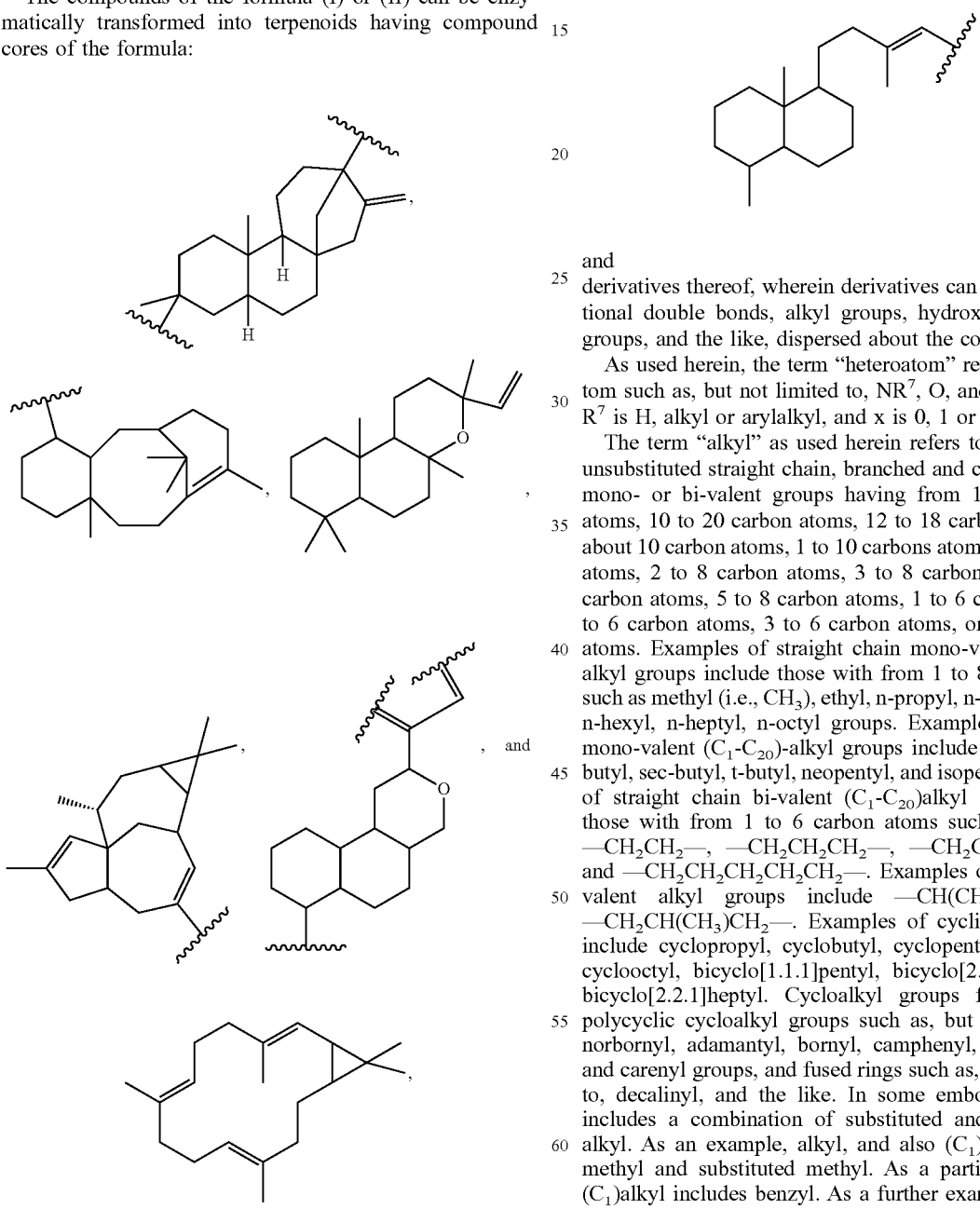

which correspond to the cores of stevioside, Taxol®, Forskolin, Picato®, and Salvinorin, Casbene, CPP respectively; or the core shared by CPP, LPP, PgPP, and KPP, namely:

and derivatives thereof, wherein derivatives can comprise additional double bonds, alkyl groups, hydroxy groups, acyl groups, and the like, dispersed about the cores.

As used herein, the term "heteroatom" refers to heteroatom such as, but not limited to, $NR^7$, O, and $SO_x$, wherein $R^7$ is H, alkyl or arylalkyl, and x is 0, 1 or 2.

The term "alkyl" as used herein refers to substituted or unsubstituted straight chain, branched and cyclic, saturated mono- or bi-valent groups having from 1 to 20 carbon atoms, 10 to 20 carbon atoms, 12 to 18 carbon atoms, 6 to about 10 carbon atoms, 1 to 10 carbons atoms, 1 to 8 carbon atoms, 2 to 8 carbon atoms, 3 to 8 carbon atoms, 4 to 8 carbon atoms, 5 to 8 carbon atoms, 1 to 6 carbon atoms, 2 to 6 carbon atoms, 3 to 6 carbon atoms, or 1 to 3 carbon atoms. Examples of straight chain mono-valent ($C_1$-$C_{20}$)-alkyl groups include those with from 1 to 8 carbon atoms such as methyl (i.e., $CH_3$), ethyl, n-propyl, n-butyl, n-pentyl, n-hexyl, n-heptyl, n-octyl groups. Examples of branched mono-valent ($C_1$-$C_{20}$)-alkyl groups include isopropyl, iso-butyl, sec-butyl, t-butyl, neopentyl, and isopentyl. Examples of straight chain bi-valent ($C_1$-$C_{20}$)alkyl groups include those with from 1 to 6 carbon atoms such as —$CH_2$—, —$CH_2CH_2$—, —$CH_2CH_2CH_2$—, —$CH_2CH_2CH_2CH_2$—, and —$CH_2CH_2CH_2CH_2CH_2$—. Examples of branched bi-valent alkyl groups include —$CH(CH_3)CH_2$— and —$CH_2CH(CH_3)CH_2$—. Examples of cyclic alkyl groups include cyclopropyl, cyclobutyl, cyclopentyl, cyclohexyl, cyclooctyl, bicyclo[1.1.1]pentyl, bicyclo[2.1.1]hexyl, and bicyclo[2.2.1]heptyl. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. In some embodiments, alkyl includes a combination of substituted and unsubstituted alkyl. As an example, alkyl, and also ($C_1$)alkyl, includes methyl and substituted methyl. As a particular example, ($C_1$)alkyl includes benzyl. As a further example, alkyl can include methyl and substituted ($C_2$-$C_8$)alkyl. Alkyl can also include substituted methyl and unsubstituted ($C_2$-$C_5$)alkyl. In some embodiments, alkyl can be methyl and $C_2$-$C_5$ linear alkyl. In some embodiments, alkyl can be methyl and $C_2$-$C_8$ branched alkyl. The term methyl is understood to be —$CH_3$, which is not substituted. The term methylene is understood to be —CH$_2$—, which is not substituted. For comparison, the term (C$_1$)alkyl is understood to be a substituted or an unsubstituted —CH$_3$ or a substituted or an unsubstituted —CH$_2$—. Representative substituted alkyl groups can be substituted one or more times with any of the groups listed herein, for example, cycloalkyl, heterocyclyl, aryl, amino, haloalkyl, hydroxy, cyano, carboxy, nitro, thio, alkoxy, and halogen groups. As further example, representative substituted alkyl groups can be substituted one or more fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido. In some embodiments, representative substituted alkyl groups can be substituted from a set of groups including amino, hydroxy, cyano, carboxy, nitro, thio and alkoxy, but not including halogen groups.

The terms "halo," "halogen," or "halide" group, as used herein, by themselves or as part of another substituent, mean, unless otherwise stated, a fluorine, chlorine, bromine, or iodine atom.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, alkenyl, alkynyl, aryl, cycloalkyl, heterocyclyl, group or the like.

The term "alkenyl" as used herein refers to substituted or unsubstituted straight chain, branched and cyclic, saturated mono- or bi-valent groups having at least one carbon-carbon double bond and from 2 to 20 carbon atoms, 10 to 20 carbon atoms, 12 to 18 carbon atoms, 6 to about 10 carbon atoms, 2 to 10 carbons atoms, 2 to 8 carbon atoms, 3 to 8 carbon atoms, 4 to 8 carbon atoms, 5 to 8 carbon atoms, 2 to 6 carbon atoms, 3 to 6 carbon atoms, 4 to 6 carbon atoms, 2 to 4 carbon atoms, or 2 to 3 carbon atoms. The double bonds can be trans or cis orientation. The double bonds can be terminal or internal. The alkenyl group can be attached via the portion of the alkenyl group containing the double bond, e.g., vinyl, propen-1-yl and buten-1-yl, or the alkenyl group can be attached via a portion of the alkenyl group that does not contain the double bond, e.g., penten-4-yl. Examples of mono-valent (C$_2$-C$_{20}$)-alkenyl groups include those with from 1 to 8 carbon atoms such as vinyl, propenyl, propen-1-yl, propen-2-yl, butenyl, buten-1-yl, buten-2-yl, sec-buten-1-yl, sec-buten-3-yl, pentenyl, hexenyl, heptenyl and octenyl groups. Examples of branched mono-valent (C$_2$-C$_{20}$)-alkenyl groups include isopropenyl, iso-butenyl, sec-butenyl, t-butenyl, neopentenyl, and isopentenyl. Examples of straight chain bi-valent (C$_2$-C$_{20}$)alkenyl groups include those with from 2 to 6 carbon atoms such as —CHCH—, —CHCHCH$_2$—, —CHCHCH$_2$CH$_2$—, and —CHCHCH$_2$CH$_2$CH$_2$—. Examples of branched bi-valent alkyl groups include —C(CH$_3$)CH— and —CHC(CH$_3$)CH$_2$—. Examples of cyclic alkenyl groups include cyclopentenyl, cyclohexenyl and cyclooctenyl. It is envisaged that alkenyl can also include masked alkenyl groups, precursors of alkenyl groups or other related groups. As such, where alkenyl groups are described it, compounds are also envisaged where a carbon-carbon double bond of an alkenyl is replaced by an epoxide or aziridine ring. Substituted alkenyl also includes alkenyl groups which are substantially tautomeric with a non-alkenyl group. For example, substituted alkenyl can be 2-aminoalkenyl, 2-alkylaminoalkenyl, 2-hydroxyalkenyl, 2-hydroxyvinyl, 2-hydroxypropenyl, but substituted alkenyl is also understood to include the group of substituted alkenyl groups other than alkenyl which are tautomeric with non-alkenyl containing groups. In some embodiments, alkenyl can be understood to include a combination of substituted and unsubstituted alkenyl. For example, alkenyl can be vinyl and substituted vinyl. For example, alkenyl can be vinyl and substituted (C$_3$-C$_8$) alkenyl. Alkenyl can also include substituted vinyl and unsubstituted (C$_3$-C$_8$)alkenyl. Representative substituted alkenyl groups can be substituted one or more times with any of the groups listed herein, for example, monoalkylamino, dialkylamino, cyano, acetyl, amido, carboxy, nitro, alkylthio, alkoxy, and halogen groups. As further example, representative substituted alkenyl groups can be substituted one or more fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido. In some embodiments, representative substituted alkenyl groups can be substituted from a set of groups including monoalkylamino, dialkylamino, cyano, acetyl, amido, carboxy, nitro, alkylthio and alkoxy, but not including halogen groups. Thus, in some embodiments, alkenyl can be substituted with a non-halogen group. In some embodiments, representative substituted alkenyl groups can be substituted with a fluoro group, substituted with a bromo group, substituted with a halogen other than bromo, or substituted with a halogen other than fluoro. For example, alkenyl can be 1-fluorovinyl, 2-fluorovinyl, 1,2-difluorovinyl, 1,2,2-trifluorovinyl, 2,2-difluorovinyl, trifluoropropen-2-yl, 3,3,3-trifluoropropenyl, 1-fluoropropenyl, 1-chlorovinyl, 2-chlorovinyl, 1,2-dichlorovinyl, 1,2,2-trichlorovinyl or 2,2-dichlorovinyl. In some embodiments, representative substituted alkenyl groups can be substituted with one, two, three or more fluoro groups or they can be substituted with one, two, three or more non-fluoro groups.

The term "alkynyl" as used herein, refers to substituted or unsubstituted straight and branched chain alkyl groups, except that at least one triple bond exists between two carbon atoms. Thus, alkynyl groups have from 2 to 50 carbon atoms, 2 to 20 carbon atoms, 10 to 20 carbon atoms, 12 to 18 carbon atoms, 6 to about 10 carbon atoms, 2 to 10 carbons atoms, 2 to 8 carbon atoms, 3 to 8 carbon atoms, 4 to 8 carbon atoms, 5 to 8 carbon atoms, 2 to 6 carbon atoms, 3 to 6 carbon atoms, 4 to 6 carbon atoms, 2 to 4 carbon atoms, or 2 to 3 carbon atoms. Examples include, but are not limited to ethynyl, propynyl, propyn-1-yl, propyn-2-yl, butynyl, butyn-1-yl, butyn-2-yl, butyn-3-yl, butyn-4-yl, pentynyl, pentyn-1-yl, hexynyl, Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "aryl" as used herein refers to substituted or unsubstituted univalent groups that are derived by removing a hydrogen atom from an arene, which is a cyclic aromatic hydrocarbon, having from 6 to 20 carbon atoms, 10 to 20 carbon atoms, 12 to 20 carbon atoms, 6 to about 10 carbon atoms or 6 to 8 carbon atoms. Examples of (C$_6$-C$_{20}$)aryl groups include phenyl, napthalenyl, azulenyl, biphenylyl, indacenyl, fluorenyl, phenanthrenyl, triphenylenyl, pyrenyl, naphthacenyl, chrysenyl, anthracenyl groups. Examples include substituted phenyl, substituted napthalenyl, substituted azulenyl, substituted biphenylyl, substituted indacenyl, substituted fluorenyl, substituted phenanthrenyl, substituted triphenylenyl, substituted pyrenyl, substituted naphthacenyl, substituted chrysenyl, and substituted anthracenyl groups. Examples also include unsubstituted phenyl, unsubstituted napthalenyl, unsubstituted azulenyl, unsubstituted biphenylyl, unsubstituted indacenyl, unsubstituted fluorenyl, unsubstituted phenanthrenyl, unsubstituted triphenylenyl, unsubstituted pyrenyl, unsubstituted naphthacenyl, unsubstituted chrysenyl, and unsubstituted anthracenyl groups. Aryl includes phenyl groups and also non-phenyl aryl groups. From these examples, it is clear that the term $(C_6-C_{20})$aryl encompasses mono- and polycyclic $(C_6-C_{20})$aryl groups, including fused and non-fused polycyclic $(C_6-C_{20})$aryl groups.

The term "heterocyclyl" as used herein refers to substituted aromatic, unsubstituted aromatic, substituted non-aromatic, and unsubstituted non-aromatic rings containing 3 or more atoms in the ring, of which, one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. In some embodiments, heterocyclyl groups include heterocyclyl groups that include 3 to 8 carbon atoms $(C_3-C_8)$, 3 to 6 carbon atoms $(C_3-C_6)$ or 6 to 8 carbon atoms $(C_6-C_8)$. A heterocyclyl group designated as a $C_2$-heterocyclyl can be a 5-membered ring with two carbon atoms and three heteroatoms, a 6-membered ring with two carbon atoms and four heteroatoms and so forth. Likewise, a $C_4$-heterocyclyl can be a 5-membered ring with one heteroatom, a 6-membered ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. Representative heterocyclyl groups include, but are not limited to piperidynyl, piperazinyl, morpholinyl, furanyl, pyrrolidinyl, pyridinyl, pyrazinyl, pyrimidinyl, triazinyl, thiophenyl, tetrahydrofuranyl, pyrrolyl, oxazolyl, imidazolyl, triazyolyl, tetrazolyl, benzoxazolinyl, and benzimidazolinyl groups. For example, heterocyclyl groups include, without limitation:

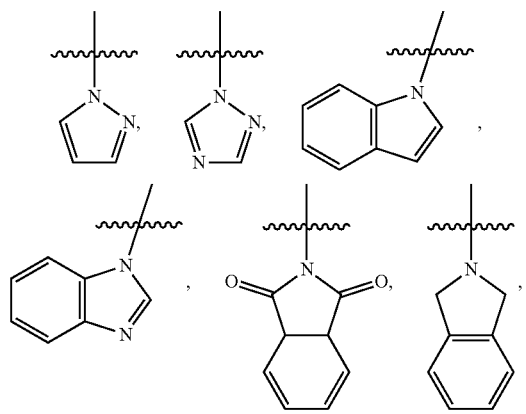

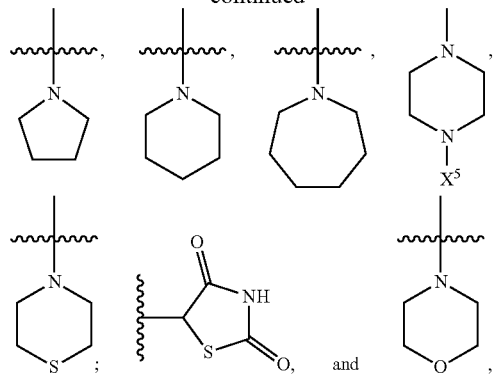

wherein
$X^5$ represents H, $(C_1-C_{20})$alkyl, $(C_6-C_{20})$aryl or an amine protecting group (e.g., a t-butyloxycarbonyl group) and wherein the heterocyclyl group can be substituted or unsubstituted. A nitrogen-containing heterocyclyl group is a heterocyclyl group containing a nitrogen atom as an atom in the ring. In some embodiments, the heterocyclyl is other than thiophene or substituted thiophene. In some embodiments, the heterocyclyl is other than furan or substituted furan.

The term "aralkyl" and "arylalkyl" as used herein refers to alkyl groups as defined herein in which a hydrogen or carbon bond of an alkyl group is replaced with a bond to an aryl group as defined herein. Representative aralkyl groups include benzyl, biphenylmethyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "substituted" as used herein refers to a group that is substituted with one or more groups including, but not limited to, the following groups: halogen (e.g., F, Cl, Br, and I), R, OR, ROH (e.g., CH2OH), OC(O)N(R)2, CN, NO, NO2, ONO2, azido, CF3, OCF3, methylenedioxy, ethylenedioxy, (C3-C20)heteroaryl, N(R)2, Si(R)3, SR, SOR, SO2R, SO2N(R)2, SO3R, P(O)(OR)2, OP(O)(OR)2, C(O)R, C(O)C(O)R, C(O)CH2C(O)R, C(S)R, C(O)OR, OC(O)R, C(O)N(R)2, C(O)N(R)OH, OC(O)N(R)2, C(S)N(R)2, (CH2)0-2N(R)C(O)R, (CH2)0-2N(R)N(R)2, N(R)N(R)C(O)R, N(R)N(R)C(O)OR, N(R)N(R)CON(R)2, N(R)SO2R, N(R)SO2N(R)2, N(R)C(O)OR, N(R)C(O)R, N(R)C(S)R, N(R)C(O)N(R)2, N(R)C(S)N(R)2, N(COR)COR, N(OR)R, C(=NH)N(R)2, C(O)N(OR)R, or C(=NOR)R wherein R can be hydrogen, (C1-C20)alkyl, (C6-C20)aryl, heterocyclyl or polyalkylene oxide groups, such as polyalkylene oxide groups of the formula —(CH2CH2O)f-R—OR, —(CH2CH2CH2O)g-R—OR, —(CH2CH2O)f(CH2CH2CH2O)g-R—OR each of which can, in turn, be substituted or unsubstituted and wherein f and g are each independently an integer from 1 to 50 (e.g., 1 to 10, 1 to 5, 1 to 3 or 2 to 5). Substituted also includes a group that is substituted with one or more groups including, but not limited to, the following groups: fluoro, chloro, bromo, iodo, amino, amido, alkyl, hydroxy, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido. Where there are two or more adjacent substituents, the substituents can be linked to form a carbocyclic or heterocyclic ring. Such adjacent groups can have a vicinal or germinal relationship, or they can be adjacent on a ring in, e.g., an ortho-arrangement. Each instance of substituted is understood to be independent. For example, a substituted aryl can be substituted with bromo and a substituted heterocycle on the same compound can be substituted with alkyl. It is envisaged that a substituted group can be substituted with one or more non-fluoro groups. As another example, a substituted group can be substituted with one or more non-cyano groups. As another example, a substituted group can be substituted with one or more groups other than haloalkyl. As yet another example, a substituted group can be substituted with one or more groups other than tert-butyl. As yet a further example, a substituted group can be substituted with one or more groups other than trifluoromethyl. As yet even further examples, a substituted group can be substituted with one or more groups other than nitro, other than methyl, other than methoxymethyl, other than dialkylaminosulfonyl, other than bromo, other than chloro, other than amido, other than halo, other than benzodioxepinyl, other than polycyclic heterocyclyl, other than polycyclic substituted aryl, other than methoxycarbonyl, other than alkoxycarbonyl, other than thiophenyl, or other than nitrophenyl, or groups meeting a combination of such descriptions. Further, substituted is also understood to include fluoro, cyano, haloalkyl, tert-butyl, trifluoromethyl, nitro, methyl, methoxymethyl, dialkylaminosulfonyl, bromo, chloro, amido, halo, benzodioxepinyl, polycyclic heterocyclyl, polycyclic substituted aryl, methoxycarbonyl, alkoxycarbonyl, thiophenyl, and nitrophenyl groups.

Hosts

Terpenes, including diterpenes and terpenoids, can be made in a variety of host organisms in vivo. In some cases, the enzymes described herein can be made in host cells, and those enzymes can be extracted from the host cells for use in vitro. As used herein, a "host" means a cell, tissue or organism capable of replication. The host can have an expression cassette or expression vector that can include a nucleic acid segment encoding an enzyme that is involved in the biosynthesis of terpenes.

The term "host cell", as used herein, refers to any prokaryotic or eukaryotic cell that can be transformed with an expression cassettes or vector carrying the nucleic acid segment encoding an enzyme that is involved in the biosynthesis of one or more terpenes or terpenoids. The host cells can, for example, be a plant, bacterial, insect, or yeast cell. Expression cassettes encoding biosynthetic enzymes can be incorporated or transferred into a host cell to facilitate manufacture of the enzymes described herein or the terpene, diterpene, or terpenoid products of those enzymes. The host cells can be present in an organism. For example, the host cells can be present in a host such as a microorganism, fungus, or plant. As illustrated herein, the host can be a plant cell such as a *Nicotiana benthamiana* host cell.

Expression of Enzymes

Also described herein are expression systems that include at least one expression cassette (e.g., expression vectors or transgenes) that encode one or more of the enzyme(s) described herein. For example, the expression systems can also include one or more expression cassettes any of the monoterpene synthase, diterpene synthase, sesquiterpene synthase, sesterterpene synthase, triterpene synthase, tetraterpene synthase, polyterpene synthase, transcription factor, cis-prenyl transferase, terpene synthase, cytochrome P450 (CYP71D616), cytochrome P450 reductase, 1-deoxy-D-xylulose 5-phosphate synthase (DXS), 1-deoxy-D-xylulose 5-phosphate-reducto-isomerase, cytidine 5'-diphosphate-methylerythritol (CDP-ME) synthetase (IspD), 2-C-methyl-d-erythritol 2,4-cyclodiphosphate synthase (IspF), HMG-CoA synthase, HMG-CoA reductase (HMGR), mevalonic acid kinase (MVK), phosphomevalonate kinase (PMK), mevalonate-5-diphosphate decarboxylase (MPD), isopentenyl diphosphate isomerase, abietadiene synthase (ABS), farnesylpyrophosphate synthase (FPPS), or squalene synthase (SOS), LDSP-protein fusions, or enzymes that facilitate production of terpenoids, terpene precursors, terpene building blocks, or products derived from terpenoids.

Nucleic acids encoding the enzymes can have sequence modifications. For example, nucleic acid sequences described herein can be modified to more optimally express the enzymes. Hence, the nucleic acid segment encoding the enzymes can be optimized to improve expression in different host cells. Most amino acids can be encoded by more than one codon, but when an amino acid is encoded by more than one codon, the codons are referred to as degenerate codons. A listing of degenerate codons is provided in Table 1B below.

TABLE 1B

Degenerate Amino Acid Codons

| Amino Acid | Three Nucleotide Codon |
|---|---|
| Ala/A | GCT, GCC, GCA, GCG |
| Arg/R | CGT, CGC, CGA, CGG, AGA, AGG |
| Asn/N | AAT, AAC |
| Asp/D | GAT, GAC |
| Cys/C | TGT, TGC |
| Gln/Q | CAA, CAG |
| Glu/E | GAA, GAG |
| Gly/G | GGT, GGC, GGA, GGG |
| His/H | CAT, CAC |
| Ile/I | ATT, ATC, ATA |
| Leu/L | TTA, TTG, CTT, CTC, CTA, CTG |
| Lys/K | AAA, AAG |
| Met/M | ATG |
| Phe/F | TTT, TTC |
| Pro/P | CCT, CCC, CCA, CCG |
| Ser/S | TCT, TCC, TCA, TCG, AGT, AGC |
| Thr/T | ACT, ACC, ACA, ACG |
| Trp/W | TGG |
| Tyr/Y | TAT, TAG |
| Val/V | GTT, GTC, GTA, GTG |
| START | ATG |
| STOP | TAG, TGA, TAA |

Different organisms may translate different codons more or less efficiently (e.g., because they have different ratios of tRNAs) than other organisms. Hence, when some amino acids can be encoded by several codons, a nucleic acid segment can be designed to optimize the efficiency of expression of an enzyme by using codons that are preferred by an organism of interest. For example, the nucleotide coding regions of the enzymes described herein can be codon optimized for expression in various microorganisms, fungi, or plant species.

An optimized nucleic acid can have less than 100%, less than 99%, less than 98%, less than 97%, less than 95%, or less than 94%, or less than 93%, or less than 92%, or less than 91%, or less than 90%, or less than 89%, or less than 88%, or less than 85%, or less than 83%, or less than 80%, or less than 75% nucleic acid sequence identity to a corresponding non-optimized (e.g., a non-optimized parental or wild type enzyme nucleic acid) sequence. Nucleic acid segment(s) encoding one or more enzyme(s) can therefore have one or more nucleotide deletions, insertions, replacements, or substitutions.

The nucleic acid segments encoding one or more enzyme can be operably linked to a promoter, which provides for expression of mRNA from the nucleic acid segments. The promoter is typically a promoter functional in a microorganism, fungus or plant. A nucleic acid segment encoding one or more enzyme is operably linked to the promoter, for example, when it is located downstream from the promoter. The combination of a coding region for an enzyme operably linked to a promoter forms an expression cassette, which can include other elements and regulatory sequences as well.

Promoter regions are typically found in the flanking DNA upstream from the coding sequence in both the prokaryotic and eukaryotic cells. A promoter sequence provides for regulation of transcription of the downstream gene sequence and typically includes from about 50 to about 2,000 nucleotide base pairs. Promoter sequences can also contain regulatory sequences such as enhancer sequences that can influence the level of gene expression. Some isolated promoter sequences can provide for gene expression of heterologous DNAs, that is a DNA different from the native or homologous DNA.

Promoter sequences are also known to be strong or weak, or inducible. A strong promoter provides for a high level of gene expression, whereas a weak promoter provides for a very low level of gene expression. An inducible promoter is a promoter that provides for the turning on and off of gene expression in response to an exogenously added agent, or to an environmental or developmental stimulus. For example, a bacterial promoter such as the Ptac promoter can be induced to varying levels of gene expression depending on the level of isopropyl-beta-D-thiogalactoside added to the transformed cells. Promoters can also provide for tissue specific or developmental regulation. An isolated promoter sequence that is a strong promoter for heterologous DNAs is often advantageous because it provides for a sufficient level of gene expression for easy detection and selection of transformed cells and provides for a high level of gene expression when desired.

Examples of prokaryotic promoters that can be used include, but are not limited to, SP6, T7, T5, tac, bla, trp, gal, lac, or maltose promoters. Examples of eukaryotic promoters that can be used include, but are not limited to, constitutive promoters, e.g., viral promoters such as CMV, SV40 and RSV promoters, as well as regulatable promoters, e.g., an inducible or repressible promoter such as the tet promoter, the hsp70 promoter and a synthetic promoter regulated by CRE.

Examples of plant promoters include the CaMV 35S promoter (Odell et al., Nature. 313:810-812 (1985)), or others such as CaMV 19S (Lawton et al., Plant Molecular Biology. 9315-324 (1987)), nos (Ebert et al., Proc. Natl. Acad. Sci. USA. 84:5745-5749 (1987)), Adh1 (Walker et al., Proc. Natl. Acad. Sci. USA. 84:6624-6628 (1987)), sucrose synthase (Yang et al., Proc. Natl. Acad. Sci. USA. 87:4144-4148 (1990)), α-tubulin, ubiquitin, actin (Wang et al., Mol. Cell. Biol. 123399 (1992)), cab (Sullivan et al., Mol. Gen. Genet. 215:431 (1989)), PEPCase (Hudspeth et al., Plant Molecular Biology. 12:579-589 (1989)) or those associated with the R gene complex (Chandler et al., The Plant Cell. 1:1175-1183 (1989)). Further suitable promoters include a CYP71D16 trichome-specific promoter and the CBTS (cembratrienol synthase) promotor, cauliflower mosaic virus promoter, the Z10 promoter from a gene encoding a 10 kD zein protein, a Z27 promoter from a gene encoding a 27 kD zein protein, the plastid rRNA-operon (rrn) promoter, inducible promoters, such as the light inducible promoter derived from the pea rbcS gene (Coruzzi et al., EMBO J. 3:1671 (1971)), RUBISCO-SSU light inducible promoter (SSU) from tobacco and the actin promoter from rice (McElroy et al., The Plant Cell. 2:163-171 (1990)). Other promoters that are useful can also be employed.

Examples of leaf-specific promoters include the promoter from the *Populus* ribulose-1,5-bisphosphate carboxylase small subunit gene (Wang et al. Plant Molec Biol Reporter 31 (1): 120-127 (2013)), the promoter from the Brachypodium distachyon sedoheptulose-1,7-bisphosphatase (SBPase-p) gene (Alotaibi et al. Plants 7(2): 27 (2018)), the fructose-1,6-bisphosphate aldolase (FBPA-p) gene from Brachypodium distachyon (Alotaibi et al. Plants 7(2): 27 (2018)), and the photosystem-II promoter (CAB2-p) of the rice (*Oryza sativa* L.) light-harvest chlorophyll a/b binding protein (CAB) (Song et al. J Am Soc Hort Sci 132(4): 551-556 (2007)). Additional promoters that can be used include those available in expression databases, see for example, website bar.utoronto.ca/eplant/ which includes poplar or heterologous promoters from *Arabidopsis* (for example from AT2G26020/PDF1.2b or AT5G44420/LCR77).

Alternatively, novel tissue specific promoter sequences may be employed. cDNA clones from a particular tissue can be isolated and those clones which are expressed specifically in that tissue can be identified, for example, using Northern blotting. Preferably, the gene isolated is not present in a high copy number but is relatively abundant in specific tissues. The promoter and control elements of corresponding genomic clones can then be localized using techniques well known to those of skill in the art.

Plant plastid originated promoters can also be used, for example, to improve expression in plastids, for example, a rice clp promoter, or tobacco rrn promoter. Chloroplast-specific promoters can also be utilized for targeting the foreign protein expression into chloroplasts. For example, the 16S ribosomal RNA promoter (Prrn) like psbA and atpA gene promoters can be used for chloroplast transformation.

A nucleic acid encoding one or more enzyme can be combined with the promoter by standard methods to yield an expression cassette, for example, as described in Sambrook et al. (Molecular Cloning: A Laboratory Manual. Second Edition (Cold Spring Harbor, NY: Cold Spring Harbor Press (1989); Molecular Cloning: A Laboratory Manual. Third Edition (Cold Spring Harbor, NY: Cold Spring Harbor Press (2000)). Briefly, a plasmid containing a promoter such as the 35S CaMV promoter or the CYP71D16 trichome-specific promoter can be constructed as described in Jefferson (Plant Molecular Biology Reporter 5:387-405 (1987)) or obtained from Clontech Lab in Palo Alto, California (e.g., pBI121 or pBI221). Typically, these plasmids are constructed to have multiple cloning sites having specificity for different restriction enzymes downstream from the promoter.

The expression cassette or vector can include nucleic acid sequence encoding a marker product. This marker product is used to determine if the gene has been delivered to the cell and once delivered is being expressed. Marker genes can include the *E. coli* lacZ gene which encodes β-galactosidase, and green fluorescent protein. In some embodiments the marker can be a selectable marker. When such selectable markers are successfully transferred into a host cell, the transformed host cell can survive if placed under selective pressure. There are two widely used distinct categories of selective regimes. The first category is based on a cell's metabolism and the use of a mutant cell line which lacks the ability to grow independent of a supplemented media. The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B. et al., Mol. Cell. Biol. 5: 410-413 (1985)).

The expression cassettes can be within vectors such as plasmids, viral vectors, viral nucleic acids, phage nucleic acids, phages, cosmids, or artificial chromosomes.

Transfer of the expression cassettes or vectors into host cells can be by methods available in the art and readily adaptable for use in the method described herein. Expression cassettes and vectors can be incorporated into host cells, for example, calcium-mediated transformation, electroporation, microinjection, lipofection, particle bombardment, chemical transfectants, physico-mechanical methods such as electroporation, or direct diffusion of DNA.

Methods

Methods are described herein that are useful for synthesizing terpenoids and products made from terpenoids. The methods can involve contacting one or more of the substrates described herein with one or more enzymes capable of synthesizing at least one terpene to produce a terpenoid product. In some cases, the methods can involve incubating one or more of the substrates described herein with a population of host cells having a at least one heterologous expression cassette or expression vector that can express one or more enzymes capable of synthesizing at least one terpenoid product. The enzymes capable of synthesizing at least one terpenoid product can be referred to as a primary enzyme. The methods can also involve contacting the terpenoid product with a secondary enzyme that can modify the terpenoid product into another useful product.

For example, one method can involve contacting one or more of the substrates described herein with one or more enzymes capable of synthesizing at least one terpene to produce a terpenoid product.

For example, another method can involve (a) incubating a population of host cells or host tissue that includes one or more expression cassettes (or vectors) that have a promoter operably linked to a nucleic acid segment encoding an enzyme capable of synthesizing at least one terpene; and (b) isolating at least one terpenoid product from the population of host cells or the host tissue.

The enzymes can be any of the enzymes described herein. For example, the enzymes can be a monoterpene synthase, diterpene synthase, sesquiterpene synthase, sesterterpene synthase, triterpene synthase, tetraterpene synthase, or polyterpene synthase. Enzymes used for modifying a terpenoid product (e.g., secondary enzymes) can include one or more transcription factor, cis-prenyl transferase, terpene synthase, cytochrome P450 (CYP71D616), cytochrome P450 reductase, 1-deoxy-D-xylulose 5-phosphate synthase (DXS), 1-deoxy-D-xylulose 5-phosphate-reductoisomerase, cytidine 5'-diphosphate-methylerythritol (CDP-ME) synthetase (IspD), 2-C-methyl-d-erythritol 2,4-cyclodiphosphate synthase (IspF), geranylgeranyl diphosphate synthase (GGDPS), HMG-CoA synthase, HMG-CoA reductase (HMGR), mevalonic acid kinase (MVK), phosphomevalonate kinase (PMK), mevalonate-5-diphosphate decarboxylase (MPD), isopentenyl diphosphate isomerase (IDI), abietadiene synthase (ABS), farnesylpyrophosphate synthase (FPPS), ribulose bisphosphate carboxylase, squalene synthase (SQS), patchoulol synthase, or WRI1 protein; and (b) isolating useful products from the population of host cells, the host plant's cells, or the host tissue. In some cases, a combination of enzymes, transcription factors, and lipid droplet proteins can be expressed in host cells, host plant, or host tissues.

Definitions

As used herein, the singular forms "a," "an," and "the" are intended to include the plural forms as well, unless the context dearly indicates otherwise. Also, as used herein, "and/or" refers to, and encompasses, any and all possible combinations of one or more of the associated listed items. Unless otherwise defined, all terms, including technical and scientific terms used in the description, have the same meaning as commonly understood by one of ordinary skill in the art to which this invention pertains.

The term "about", as used herein, can allow for a degree of variability in a value or range, for example, within 10%, within 5%, or within 1% of a stated value or of a stated limit of a range.

The term "enzyme" or "enzymes", as used herein, refers to a protein catalyst capable of catalyzing a reaction. Herein, the term does not mean only an isolated enzyme, but also includes a host cell expressing that enzyme. Accordingly, the conversion of A to B by enzyme C should also be construed to encompass the conversion of A to B by a host cell expressing enzyme C.

The term "heterologous" when used in reference to a nucleic acid refers to a nucleic acid that has been manipulated in some way. For example, a heterologous nucleic acid includes a nucleic acid from one species introduced into another species. A heterologous nucleic acid also includes a nucleic acid native to an organism that has been altered in some way (e.g., mutated, added in multiple copies, linked to a non-native promoter or enhancer sequence, etc.). Heterologous nucleic acids can include cDNA forms of a nucleic acid; the cDNA may be expressed in either a sense (to produce mRNA) or anti-sense orientation (to produce an anti-sense RNA transcript that is complementary to the mRNA transcript). For example, heterologous nucleic acids can be distinguished from endogenous plant nucleic acids in that the heterologous nucleic acids are typically joined to nucleic acids comprising regulatory elements such as promoters that are not found naturally associated with the natural gene for the protein encoded by the heterologous gene. Heterologous nucleic acids can also be distinguished from endogenous plant nucleic acids in that the heterologous nucleic acids are in an unnatural chromosomal location or are associated with portions of the chromosome not found in nature (e.g., the heterologous nucleic acids are expressed in tissues where the gene is not normally expressed).

The terms "identical" or percent "identity", as used herein, in the context of two or more nucleic acids or polypeptide sequences, refer to two or more sequences or subsequences that are the same or have a specified percentage of amino acid residues or nucleotides that are the same (e.g., 75% identity, 80% identity, 85% identity, 90% identity, 95% identity, 97% identity, 98% identity, 99% identity, or 100% identity in pairwise comparison). Sequence identity can be determined by comparison and/or alignment of sequences for maximum correspondence over a comparison window, or over a designated region as measured using a sequence comparison algorithm, or by manual alignment and visual inspection. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. A "reference sequence" is a defined sequence used as a basis for a sequence comparison; a reference sequence may be a subset of a larger sequence.

As used herein, a "native" nucleic acid or polypeptide means a DNA, RNA, or amino acid sequence or segment thereof that has not been manipulated in vitro, i.e., has not been isolated, purified, amplified and/or modified.

The terms "in operable combination," "in operable order," and "operably linked" refer to the linkage of nucleic acid sequences in such a manner that a nucleic acid molecule capable of directing the transcription of a coding region (e.g., gene) and/or the synthesis of a desired protein molecule is produced. The term also refers to the linkage of amino acid sequences in such a manner so that a functional protein is produced.

As used herein the term "terpene" includes any type of terpene or terpenoid, including for example any monoterpene, diterpene, sesquiterpene, sesterterpene, triterpene, tetraterpene, polyterpene, and any mixture thereof.

As used herein, the term "wild-type" when made in reference to a gene refers to a functional gene common throughout an outbred population. As used herein, the term "wild-type" when made in reference to a gene product refers to a functional gene product common throughout an outbred population. A functional wild-type gene is that which is most frequently observed in a population and is thus arbitrarily designated the "normal" or "wild-type" form of the gene.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

EXAMPLES

The present disclosure can be better understood by reference to the following examples which are offered by way of illustration and which are described in *Plant J.* 2020 November; 104(3):693-705, which is incorporated by reference as if fully set forth herein. The disclosure is not limited to the examples given herein.

Materials and Methods

Plant Material, RNA Isolation and cDNA Synthesis, and Metabolite Analysis

*Leucophyllum frutescens* plants were obtained from Stokes Tropicals (Homestead, FL, USA) and grown in a greenhouse under ambient photoperiod and 24° C. day/17° C. night temperatures. Total RNA from flower, leaf, and root tissues was extracted following methods described in *Plant Physiol.* 157, 1677-1695 (2011) using the Spectrum™ Plant Total RNA Kit (Sigma-Aldrich, St. Louis, MO, USA). RNA extraction was followed by DNase I digestion using DNA-Free™ DNA Removal Kit (ThermoFisher Scientific). Total RNA was assessed for quantity and integrity by Qubit™ (ThermoFisher Scientific) and RNA-nano assays (Agilent Bioanalyzer 2100), prior to whole transcriptome sequencing (Novogene, Sacramento, CA, USA) First-strand cDNA was synthesized from 2 µg of root total RNA using SuperScript III (Invitrogen). For GC-MS-based metabolomics, approximately 1 g of root, leaf, or flower tissue was extracted in 1 mL MTBE for 3 hours and analyzed by GC-MS with the same method described below for analysis of enzyme assays.

*L. Frutescens* and *E. Serrulata* De Novo Transcriptome Assembly and Analysis

RNA-seq data were obtained through tissue-specific RNA sequencing on an Illumina HiSeq 4000 for *L. frutescens* and the NCBI Sequence Read Archive (https://www.ncbi.nlm.nih.gov/sra (ERX1321488)) for *E. serrulata Phytochemistry* 136, 15-22 (2017). Quality of sequencing data was checked with FastQC (v0.11.4), and adapters were trimmed with Trimmomatic (v0.39; *Bioinformatics* 30, 2114-2120 (2014). A transcriptome was assembled with Trinity (v2.8.4; *Nat Biotechnol* 29, 644-652 (2011)), expression levels calculated with Salmon (v.0.11.2; *Nat. Methods* 14, 417-419 (2017)), and open reading frames picked out with TransDecoder (v5.5.0; *Nat Protoc* 8, 1494-1512 (2013)). A BLAST (v2.7.1+) search against reference databases of respective enzyme families (Dataset S1) was done to pick out candidates. Phylogenetic trees were made with Clustal Omega (v1.2.4; *Mol. Syst. Biol.* 7, 539 (2011)) and RAxML (v8.0.0; *Bioinformatics* 30, 1312-1313 (2014)) and visualized with Interactive Tree of Live (*Nucleic Acids Res* 47, W256-W259 (2019)). Plastidial transit peptides were predicted between TargetP (v 1.1; *Journal of Molecular Biology* 300, 1005-1016 (2000)) and sequence alignments with Clustal Omega (v1.2.4; *Mol. Syst. Biol.* 7, 539 (2011)).

Cloning and Sources of Genes Used

Synthetic oligonucleotides, GenBank accession numbers, and sequences of each enzyme characterized in this study are listed in Dataset S1. Candidate enzymes were PCR-amplified from root cDNA, and coding sequences were cloned through In-Fusion cloning into the plant expression vector pEAQ-HT (*Plant Biotechnol. J.* 7, 682-693 (2009)) for transient expression assays in *N. benthamiana*, or into pET-28b(+) for expression in *E. coli*. LfTPS1 and LfTPS2 were cloned into pET-28b(+) as N-terminal truncated constructs omitting the first 23 amino acid residues, removing their putative transit peptides. For in vitro assays, constructs for PvTPS4, PvTPS5, and PvHVS(Δ43) in pET-28b(+) made in *New Phytologist* 223, 323-335 (2019b) were used as positive controls. For in vivo *E. coli* assays, the same truncated LfTPS constructs described above were used. TPS constructs were co-transformed with pIRS (*Applied Micro-* biology and Biotechnology, 85(6), 1893-1906 (2010)) and pNN (New Phytologist 223, 323-335 (2019b)).

For all assays in N. benthamiana, full-length candidates were cloned into pEAQ-HT. For cytosolic tests, TPS candidates were co-expressed with Euphorbia lathyris HMGR and Methanothermobacter thermautotrophicus GGPPS (Sadre et al. 2019) in the pEarlygate vector (The Plant Journal, 45(4), 616-629 (2006)). As a positive control for cytosolic tests, an N-terminal truncated construct of PvHVS (PvHVS (Δ43)) was cloned into pEAQ-HT in this study. For plastidial tests, each candidate was coexpressed with Coleus forskohlii DXS (Angewandte Chemie International Edition 55, 2142-2146 (2016)) in pEarlygate. TPS candidate tests involved either co-expression of C. forskohlii GGPPS (Angewandte Chemie International Edition 55, 2142-2146 (2016)) in pEarlygate or Solanum lycopersicum CPT2 in pEAQ-HT (New Phytologist 223, 323-335 (2019b)), with a full-length construct of PvHVS in pEAQ-HT as a positive control (New Phytologist 223, 323-335 (2019b)).

In Vitro Assays

TPS expression and purification was carried out as described in New Phytologist 223, 323-335 (2019b). LfTPS1 and LfTPS2 constructs in pET-28b(+) were transformed into the E. coli C41 OverExpress strain. Primary cultures (5 mL LB plus 50 µg/mL kanamycin) were grown overnight 37° C., and 1 mL was used to inoculate a bulk culture (100 mL TB plus 50 µg/mL kanamycin). This culture was grown to an $OD_{600}$ of 0.6 at 37° C., and expression was induced with 0.2 mM IPTG. Expression was carried out overnight at 17° C., cells were collected by centrifugation, and resuspended in Buffer A (20 mM HEPES, pH 7.2, 25 mM imidazole, 500 mM NaCl, 5% (v/v) glycerol) plus 10 µL/ml protease inhibitor cocktail (Sigma) and 0.1 mg/ml lysozyme (VWR). Cells were lysed by sonication and centrifuged at 11,000×g for 30 min. Supernatants were loaded onto Ni-NTA columns (His Spin-Trap; GE Healthcare) preequilibrated with Buffer A, washed with two column volumes of Buffer A, and protein was eluted with Buffer B (Buffer A with 350 mM imidazole). Samples were de-salted with a PD MidiTrap G-25 column (GE Healthcare) pre-equilibrated with Buffer C (20 mM HEPES, pH 7.2, 1 mM $MgCl_2$, 350 mM NaCl, and 5% (v/v) glycerol). Purified enzymes were frozen in liquid nitrogen and stored at −80° C. prior to in vitro assays.

In vitro assays were carried out with 1 µM enzyme and 30 µM substrate (GPP, FPP, or GGPP; Cayman Chemical) in 750 µL Buffer D (50 mM HEPES, pH 7.2, 7.5 mM $MgCl_2$, and 5% (v/v) glycerol), with 500 uL hexane overlay. Reactions were carried out for 16 hours at 30° C., vortexed to extract products, and centrifuged to re-separate the aqueous and organic layers. The organic layer was directly removed for GC-MS analysis.

Transient Expression in N. Benthamiana

Transient expression assays in N. benthamiana were carried out as described earlier (J. Biol. Chem., jbc.RA118.006025 (2019a)). N. benthamiana plants were grown for 5 weeks in a controlled growth room under 16 h light (24° C.) and 8 h dark (17° C.) cycle before infiltration. Constructs of candidates in pEAQ and others used for co-expression were separately transformed into Agrobacterium tumefaciens strain LBA4404. Cultures were grown overnight at 30° C. in 10 mL LB plus 50 µg/mL kanamycin and 50 µg/mL rifampicin, collected by centrifugation, and washed with 10 mL water twice. Cells were resuspended and diluted to an $OD_{600}$ of 1.0 in water plus 200 µM acetosyringone and incubated at 30° C. for 2-3 hours. Separate cultures were mixed in a 1:1 ratio for each combination of enzyme tested (e.g. for leubethanol production, equal volumes of cultures were mixed harboring CfDXS, LfCPT1, LfTPS1, and CYP71D616). Mixed cultures were infiltrated with a syringe into the abaxial side of N. benthamiana leaves, and plants were returned to the controlled growth room for 5 days. Approximately 200 mg fresh weight from infiltrated leaves was extracted with 1 mL hexane overnight at 18° C., plant material was collected by centrifugation, and the organic phase was removed for GC-MS analysis.

E. coli In Vivo Assays

For in vivo E. coli assays, an engineered E. coli system (J. Am. Chem. Soc. 129, 6684-6685 (2007)) was used. LfTPS1 (Δ23) and LfTPS2(Δ23) were co-transformed with pIRS and pNN and grown overnight at 37° C. in 5 mL LB plus 25 µg/mL kanamycin, 17 µg/mL chloramphenicol, and 25 µg/mL streptomycin. A culture of 10 mL TB including the same antibiotics (same concentrations) was inoculated with 100 µL of the overnight culture and grown to an OD600 of 0.6 at 37° C. The incubation temperature was lowered to 16° C. for 1 hour, expression was induced with 0.5 mM IPTG, and cultures were supplemented with 1 mM $MgCl_2$ and 40 mM pyruvate. Cultures were incubated at 16° C. for an additional 60 hours before extraction with an equal volume of hexane and 2% (v/v) EtOH. The organic phase was separated by centrifugation and analyzed by GC-MS.

Dihydroserrulatene Production Scale-Up and NMR

To generate enough of the major LfTPS1 product (dihydroserrulatene) for NMR analysis, production in the E. coli system was carried out as detailed above, scaled up to 1 L. Following extraction, the organic layer was separated by centrifugation, concentrated under $N_2$ gas, and analyzed by GC-MS to confirm the presence of the LfTPS1 product. This product was purified by silica gel flash column chromatography with a mobile phase of 10% ethyl acetate in hexane. NMR spectra were measured on an Agilent DirectDrive2 500 MHz spectrometer using $CDCl_3$ as the solvent. CDCl3 peaks were referenced to 7.26 and 77.00 ppm for $^1H$ and $^{13}C$ spectra, respectively.

GC-MS

All GC-MS analyses were performed on an Agilent 7890A GC with an Agilent VF-5ms column (30 m×250 µm×0.25 µm, with 10 m EZ-Guard) and an Agilent 5975C detector. The inlet was set to 250° C. splitless injection of 1 µL, He carrier gas (1 ml/min), and the detector was activated following a 3 min solvent delay. All assays and tissue analysis, with the exception of in vitro assays against GPP, used the following method: temperature ramp start 40° C., hold 1 min, 40° C./min to 200° C., hold 4.5 min, 20° C./min to 240° C., 10° C./min to 280° C.; 40° C./min to 320° C.; hold 5 min (3 min hold for in vitro assays). For in vitro assays against GPP, the following method was used: temperature ramp start 40° C.; 10° C./min to 180° C.; 40° C./min to 320° C.; hold 3 min.

Homology Modeling

Homology models for LfCPT1 were generated using I-TASSER (v. 5.1; Nat. Methods 12, 7-8 (2015)) with either Solanum habrochaites (Z-2)-FPPS (PDB ID: 5HXN; ACS Omega 2, 930-936 (2017)) or LiLPPS (PDB ID: 5HC6; Angewandte Chemie International Edition 55, 4721-4724 (2016)) as the template structure. Figures were generated in PyMOL (v2.3).

Data Availability

RNA-seq data for L. frutescens has been submitted to the NCBI Sequence Read Archive (SRA) under the accession numbers SRX8371655 (root) and SRX8371656 (flower). GenBank accession numbers for nucleotide sequences of all enzymes tested in this study are as follows: LfTPS1:

MT136608; LfTPS2: MT136609; LfCPT1: MT136610; LfCPT2: MT136611; LfCPT3: MT136612; CYP706G22: MT136613; CYP76A112: MT136614; CYP736A294: MT136615; CYP736A295: MT136616; CYP71D615: MT136617; CYP71D616: MT136618 EsTPS1: MT136619. Additional L. frutescens class I TPS candidates which were cloned but not characterized: LfTPS3: MT521506; LfTPS5: MT521507; LfTPS6: MT521505; LfTPS7: MT521508; LfTPS8a: MT521515; LfTPS8b: MT521516; LfTPS9: MT521509; LfTPS10: MT521511; LfTPS11: MT521510; LfTPS12a: MT521512; LfTPS12b: MT521513; LfTPS13: MT521514.

Example 1: Accumulation of Leubethanol Guided Tissue-Specific RNA Sequencing

To begin the search for the biosynthetic pathway to leubethanol, the inventor(s) took advantage of its tissue-specific accumulation in L. frutescens. Previous work on the medicinal properties of this species has shown that root extracts were most potent against multi-drug-resistant tuberculosis, while leaves showed some activity and flowers showed none (*Journal of Ethnopharmacology* 109, 435-441 (2007)). To confirm the tissue-specific accumulation of leubethanol, extracts of the leaves, roots, and flowers were analyzed by GC-MS. Leubethanol was found to accumulate in both root and leaf tissue, while none was detected in flower tissue. Consequently, we isolated and sequenced RNA from both the roots and flowers to allow for comparative transcriptomics between tissue types. Serrulatane diterpenoids are also found in the closely related *Eremophila* genus. *Phytochemistry* 35, 7-33 (1993). RNA-seq data are publicly available from the leaves of *E. serrulata* (SRA: ERX1321488; (*Phytochemistry* 136, 15-22 (2017)) and serrulatanes are known to accumulate in this tissue (Ndi, 2007b). These data were also included to allow for comparison between genera.

Example 2: Identification of TPS Candidates from L. Frutescens

The search began by identifying TPS candidates from L. frutescens through a homologybased search of our transcriptomic data against a reference set of TPSs.

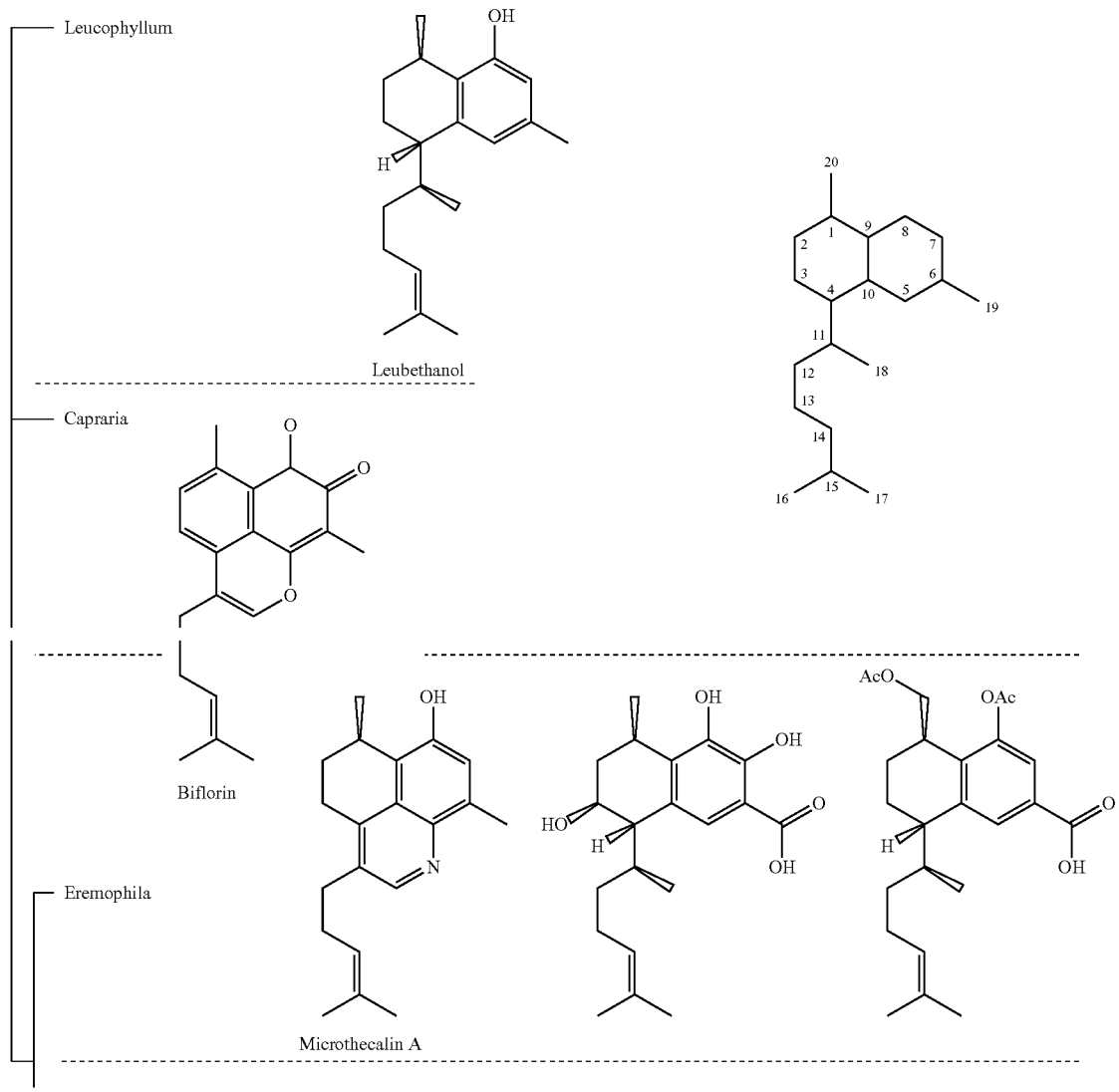

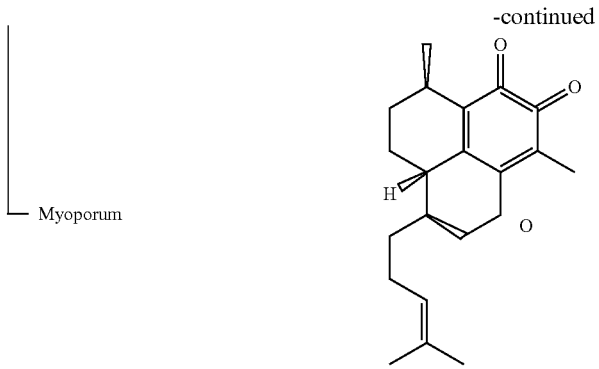
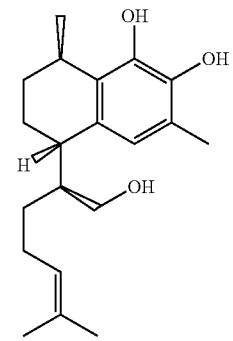

Myoporum

Fifteen candidates were identified, and a phylogenetic tree was constructed to group each candidate by TPS subfamily. One candidate (LfTPS13) was not expressed in root tissue and was eliminated from further consideration.

While containing a bicyclic decalin core, the structure of leubethanol is inconsistent with the labdane group of plant diterpenoids, the most common type of backbone which results from cyclization by pairs of class II and class I diTPS (Nat Prod Rep 27, 1521-1530 (2010)). In contrast, the cyclization pattern of leubethanol indicates activity of a class I enzyme, which catalyzes cyclization via removal of the diphosphate moiety. Out of the fourteen root-expressed candidates, only one was predicted to be a class II TPS (LfTPS4; TPS-c subfamily), and therefore thirteen possibilities remained.

A number of non-labdane diterpenes have been shown previously to be made by TPS-a enzymes which are localized to the plastid (PNAS 91, 8497-8501 (1994)). The majority of TPS-a enzymes are sesquiterpene synthases localized to the cytosol (The Plant Journal 66, 212-229 (2011)), and the presence of an N-terminal plastidial transit peptide in the primary amino acid sequence can therefore aid in prediction of diterpene synthase activity in this subfamily. Two L. frutescens candidates (LfTPS1 and LfTPS2) in the TPS-a subfamily were found to carry N-terminal extensions. Additionally, both have an ortholog in E. serrulata with nearly identical sequence length and homology through these N-terminal extensions. Of these two candidates, only LfTPS1 is exclusively expressed in root tissue and was therefore considered the more likely candidate, however both were tested.

Full-length genes for both LfTPS1 and LfTPS2 were cloned from root cDNA for transient expression in an N. benthamiana system engineered for increased levels of the presumed substrate GGPP. N-terminal truncated constructs, removing the putative transit peptides, were cloned into pET-28b(+) for expression of pseudomature variants in E. coli. Assays were extracted with hexane and analyzed by GC-MS.

To account for uncertainty of the predicted plastidial targeting signals, transient expression assays in N. benthamiana were carried out separately with co-expression of either plastidial or cytosolic GGPP terpene precursor pathway enzymes. Co-expression of both candidates with either cytosolic or plastidial precursor enzymes did not yield detectable products. To independently verify activity, each enzyme was expressed in E. coli with a C-terminal histidine tag and purified through Ni-affinity chromatography. Consistent with the results of the transient N. benthamiana assays, incubation of both LfTPS1 and LfTPS2 with GGPP in in vitro assays yielded no measurable activity. Additionally, no activity was seen when incubated with farnesyl diphosphate (FPP, precursor for sesquiterpenes) or geranyl diphosphate (GPP, precursor for monoterpenes).

Example 3: LfTPS1 Exclusively Cyclizes Nerylneryl Diphosphate into the Serrulatane Backbone Following these results, we considered two routes forward: first, to expand testing to each other class I TPS candidate, and second, to test LfTPS1 and LfTPS2 against uncommon terpene precursors. The former route was considered because even very closely related TPSs can have activities which differ substantially and there are many examples of TPSs which have different functions than would be predicted by their subfamily. The latter route was considered because of the absence of activity against each common substrate. GPP, FPP, and GGPP contain exclusively trans double bonds. All-cis stereoisomers of each have been reported in members of the nightshade (Solanaceae) family, together with TPSs which can convert these to terpene products.

The serrulatane backbone is ambiguous with respect to the original stereochemistry of its precursor; however, closer inspection of diterpenoids from the Eremophila genus shows that acyclic, bisabolane, and cembrane type diterpenoids in various Eremophila species contain internal cis double bonds.

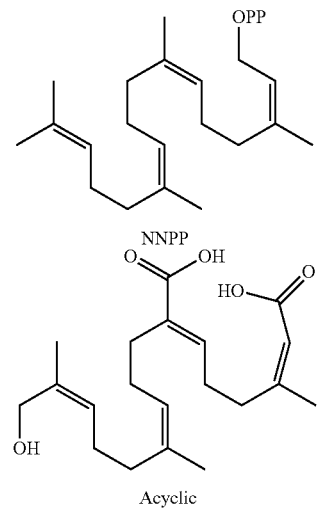

Acyclic

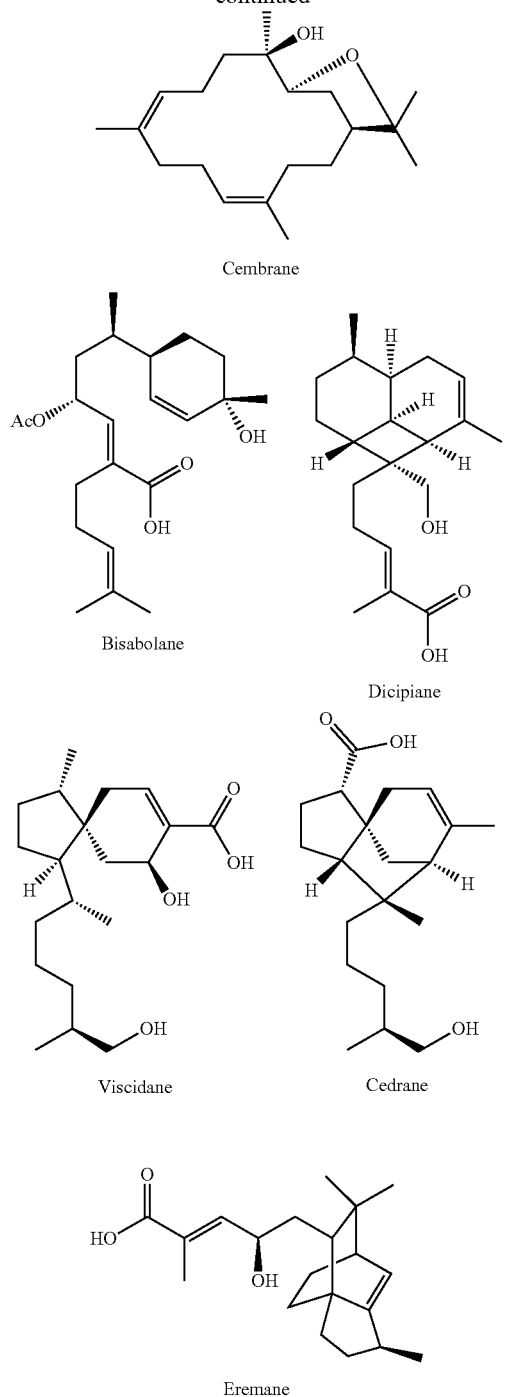

Cembrane

Bisabolane

Dicipiane

Viscidane

Cedrane

Eremane

This prompted us to test NNPP (the all-cis stereoisomer of GGPP) as the precursor for the serrulatane backbone in *L. frutescens*. Since NNPP is not commercially available, truncated constructs of LfTPS1 and LfTPS2 in pET-28b(+) were used for co-expression with SlCPT2, the plastidial *S. lycopersicum* cis-PT, in an *E. coli* system engineered to increase terpene precursor availability. Following hexane extraction and analysis by GC-MS, LfTPS1 was found to convert NNPP. This activity was independently confirmed in *N. benthamiana*. Four diterpene products were observed, with only one major product A:

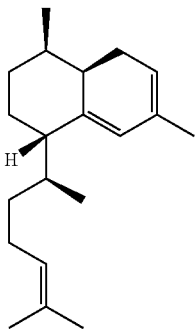

A

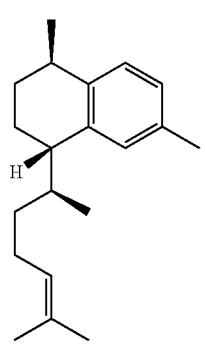

B in the *E. coli* system, and a relative amount of another compound B exceeding:

A in *N. benthamiana*. Diterpene olefins typically have a molecular ion of 272 m/z, however B has a molecular ion of 270 m/z. The fragmentation pattern for B is consistent with an aromatic product, and is similar to that of leubethanol (286 m/z) with major peaks shifted by 16, consistent with a difference of one hydroxylation. Given that TPSs are not known to catalyze redox reactions, B is likely derived from spontaneous aromatization of the major product A, a phenomenon seen previously in diterpene biosynthesis. To confirm the structure of A, production in the *E. coli* system was scaled up for NMR analysis, revealing that LfTPS1 makes dihydroserrulatene, and supporting the identity of B as serrulatene.

In parallel to the testing against NNPP, we began working towards testing the remaining class I candidate TPSs. While we cloned each of these candidates out of *L. frutescens* cDNA, we received the positive results for LfCPT1 conversion of NNPP to dihydroserrulatene before we characterized these other candidates. These were, however, cloned and sequence verified, and are given here with GenBank accession numbers for reference.

Example 3: LfCPT1, a Short Chain Cis-Prenyl Transferase, Supplies NNPP in Serrulatane Biosynthesis We next sought out the source of NNPP in *L. frutescens* by searching for a cis-prenyl transferase. Cis-PTs are ubiquitous throughout plants and are typically involved in the synthesis of long chain polyisoprenoids (Akhtar et al., 2013), although very few which make short chain products (fewer than 35 carbons) have been identified. Three short-chain cis-PTs which yield NPP (neryl diphosphate: 10 carbon), (Z-Z)-FPP (Z-Z-farnesyl diphosphate; 15 carbon), and NNPP (20 carbon) have been identified from *Solanum lycopersicum* through functional characterization of the entire family of cis-PTs from this species. We identified candidate cis-PTs from both the *L. frutescens* and *E. serrulata* transcriptomes through a homology-based search against the entire family of cis-PTs from *S. lycopersicum*. Ten candidate cis-PTs were identified from *L. frutescens*, and phylogenetic analysis revealed that six are closely related to the short-chain cis-PTs from *S. lycopersicum*. LfTPS1 has a predicted plastidial transit peptide, and successfully converts NNPP in *N. benthamiana* assays when co-expressed with SlCPT2, which is known to be targeted to the plastid. Therefore, we looked for a cis-PT candidate that is likely targeted to the plastid. Three of these candidates were found to carry predicted plastidial transit peptides and are expressed in root tissue (LfCPT1-3). LfCPT1 was considered to be the most likely candidate as it is the only of these three to have a direct ortholog in our *E. serrulata* transcriptome assembly (EsCPT1), however all three were tested.

LfCPT1-3 were cloned from *L. frutescens* root cDNA. Each candidate cis-PT was coexpressed in *N. benthamiana* with LfTPS1, and products were analyzed by GC-MS following hexane extraction. Co-expression with LfCPT1 yielded the same diterpene product profile as with the NNPP synthase from *S. lycopersicum* (SlCPT2). In addition, direct comparison of LfCPT1 with SlCPT2 without co-expression of a TPS showed the same peak and mass spectrum for dephosphorylated NNPP.

Example 4: A Cytochrome P450 Converts the Serrulatane Backbone to Leubethanol Leubethanol is oxidized twice relative to dihydroserrulatene, presumably through hydroxylation by a cytochrome P450 and aromatization. Given the propensity for dihydroserrulatene to spontaneously aromatize to serrulatene, we set out to identify P450 candidates for the required oxidation at $C_8$. A homology-based search of both the *L. frutescens* and *E. serrulata* transcriptomes was carried out against a reference set of plant P450s. 165 candidates were identified from *L. frutescens*. We first narrowed our search by focusing on those within the CYP71 clan. While P450s in other clans have been identified in diterpenoid specialized metabolism, we began our search here based on the CYP71 clan containing the majority of previously characterized examples. Clustering each P450 candidate by family and eliminating those outside of the CYP71 clan reduced the list of candidates to 59. Considering only those that were expressed in root tissue but not flower tissue, and those that had an ortholog in our *E. serrulata* transcriptome assembly, only five candidates remained. One additional candidate (CYP71D615), which did not have a direct ortholog in *E. serrulata*, was included based on its root-exclusive expression and location among a cluster of other *L frutescens* and *E. serrulata* candidates in the phylogenetic tree.

These six P450 candidates were cloned from *L. frutescens* root cDNA. Co-expression with LfCPT1 and LfTPS1 in *N. benthamiana* revealed that CYP71D616 facilitates the conversion of dihydroserrulatene to leubethanol. A relative decrease of dihydroserrulatene over serrulatene indicates that the preferred substrate for CYP71D616 is dihydroserrulatene. The observed minor reduction in serrulatene is plausibly due to P450-mediated turnover of dihydroserrulatene preceding spontaneous aromatization. This is supported by the metabolomic data from root tissue extracts, which shows an accumulation of serrulatene but no detectable quantities of dihydroserrulatene.

The interdependence of each enzyme in the pathway is demonstrated, showing that all three are necessary for leubethanol production when expressed in *N. benthamiana* To determine whether the TPS activity is conserved in the *Eremophila* genus, we tested a synthetic homolog of LfTPS1 (EsTPS1; 85% amino acid identity) from the *E. serrulata* transcriptome assembly. Replacing LfTPS1 with EsTPS1 yields the same products in each combination, demonstrating orthology between the enzymes and conservation of this pathway in the serrulatane-rich *Eremophila* genus.

DISCUSSION

Through comparative transcriptomics between tissue types and genera, we have identified three enzymes responsible for the biosynthesis of the serrulatane diterpenoid leubethanol in *L. frutescens*. The stereochemistry at all three chiral centers in dihydroserrulatene matches that of every serrulatane diterpenoid identified from the Scrophulariaceae family wherever the stereocenter is retained in the final diterpenoid product. This, and the conserved function between LfTPS1 and EsTPS1, suggest that dihydroserrulatene is in fact the common precursor to all serrulatanes. Others have reported a similar pathway to dihydroserrulatene involving a cis-PT and plastidial TPS-a in *Eremophila drummondii* and *Eremophila denticulata*, further supporting the conservation of this pathway. BMC Plant Biology 20, 91 (2020). Nearly all of the serrulatane diterpenoids in Scrophulariaceae share a common hydroxylation (or derivative thereof) with leubethanol, suggesting that leubethanol itself is a common precursor. Given this commonality, the CYP71 D616-catalyzed hydroxylation is likely the entry step between the diterpene backbone and diversification toward other antimicrobial serrulatane diterpenoids from other genera such as biflorin and microthecalin A.

This pathway is unusual in that it involves the all-cis prenyl diphosphate precursor NNPP rather than the common diterpene precursor GGPP. Prenyl diphosphate substrates are synthesized by members of either the trans- or cis-prenyl transferase families, typically in a head-to-tail condensation of the 5-carbon molecules isopentenyl diphosphate (IPP) and dimethylallyl diphosphate (DMAPP). These two enzyme families are distinct with no sequence or structural homology. The evolution of members of the cis-PT family to make uncommon terpene precursors has been found in two other cases, with the series of NPP (SlCPT1), (Z,Z)-FPP (SlCPT6), and NNPP (SlCPT2) in *S. lycopersicum* (Solanaceae), and lavandulyl diphosphate (head-to-middle condensation catalyzed by LiLPPS) in *Lavandula×intermedia* (Lamiaceae). LfCPT1, LiLPPS, and the *S. lycopersicum* short-chain cis-PT are phylogenetically closely related when compared to the overall characterized cis-PT family in *S. lycopersicum*. This may indicate a shared common ancestry of the short-chain cis-PTs in Solanaceae, Lamiaceae, and Scrophulariaceae. Scrophulariaceae diverged from Solanaceae between 75 to 88 MYA, and from Lamiaceae between 44 and 67 MYA based on molecular time estimates, which is consistent with the divergence pattern of the short-chain cis-PTs: LfCPT1 appears to be more closely related to LiLPPS (Lamiaceae) than any of the *Solanum* cis-PTs, despite being closer to the *Solanum* enzymes in product profile. Additionally, it has been suggested that the shorter product length of the *S. lycopersicum* cis-PTs may be due in part to a shortened alpha helix not present in the long-chain cis-PTs from this species. This is not present in either LiLPPS or LfCPT1 based on homology modeling and a sequence alignment, suggesting that the evolution towards smaller precursors is independent and follows different trajectories from an ancestral sequence.

In addition to finding a similar pathway to dihydroserrulatene, others have identified TPSs which make the cembrane and viscidane backbones in *Eremophila lucida*, and showed that these exclusively use NNPP over GGPP as well. To identify where the TPSs and cis-PTs from these three other *Eremophila* species (*E. denticulata, E. drummondii,* and *E. lucida*) lie relative to our candidates, we generated phylogenetic trees including each candidate identified from these species and our sequences. Each other *Eremophila* NNPP synthase is a direct ortholog of LfCPT1, while LfCPT2 and LfCPT3 have no orthologs in any of these *Eremophila* species. Interestingly, a (Z,Z)-FPP synthase (EdCPT2) was found, however a TPS in *Eremophila* which converts (Z,Z)-FPP has yet to be identified. The cembratrienol synthase (ElTPS31) is a member of the TPS-b subfamily, commonly involved in monoterpene synthesis, and *L. frutescens* does not have an ortholog. The hydroxyviscidane synthase (ElTPS3) lines up closely with LfTPS2 and another enzyme from *E. denticulata* (EdfTPS5), however neither of these candidates were found to have this same function. Interestingly, more TPSa candidates which are putatively targeted to the plastid, but do not convert GGPP or NNPP, are present in these three *Eremophila* species. The function of LfTPS2 and these other plastidial TPS-a enzymes remains to be seen, and may suggest that other precursors that were not taken into account in either study may be present in the plastids of these plants.

The identification of a short-chain cis-PT in Scrophulariaceae clarifies the likely origin of other diterpene backbones present in the *Eremophila* genus. Acyclic and bisabolane type diterpenoids identified in this genus contain internal alkenes in cis configuration. As serrulatanes and viscidanes have now both been shown to be derived from NNPP, it is likely that the decipiane, cycloserrulatane, and cedrane backbones are derived from NNPP as well. The backbones for decipianes and cycloserrulatanes resemble a tricyclic serrulatane backbone, and the cedrane backbone resembles a tricyclic viscidane backbone. Beyond Scrophulariaceae, there are hundreds of other diterpene backbones with unknown biosynthetic routes. In Lamiaceae alone there are at least 200 (Johnson et al., 2019a), and in *Salvia sclarea* (Lamiaceae), two previously reported diterpenoids salviatriene A and B (Laville et al., 2012) resemble a cycloserrulatane and tricyclic viscidane, respectively. Given the independent emergence of cis-PTs which yield NNPP in different plant families, it may be that some of these unknown diterpenoid pathways involve NNPP as well.

Numerous diterpene backbones that differ from the more common labdane structure have been shown to be formed by enzymes in the TPS-a subfamily, which is mostly comprised of cytosolic sesquiterpene synthases. LfTPS1 provides another example of a compartment and substrateswitching TPS from the this subfamily, but differs from these previous examples in that it does not convert GGPP. In contrast to earlier work in *P. vulgaris* (Lamiaceae), where the enzyme PvHVS showed acceptance of both GGPP and the presumed non-native NNPP, LfTPS1 showed a high specificity towards NNPP. PvTPS5 and PvTPS2 (both TPS-a) could also convert NNPP to a diterpene product in addition to their native functions as sesquiterpene and diterpene synthases, respectively. This could plausibly arise from negative selection against GGPP, as both substrates are available in *L. frutescens* and presumably only GGPP is available in *P. vulgaris*. The presence of competing substrates in *L. frutescens* may introduce a strong selective pressure for specificity (Tawfik, 2014), while the absence of NNPP in *P. vulgaris* means that no such selective pressure exists. Such specificity can also be seen in *Solanum* where these all-cis substrates are present, where PHS1, SBS, and SlTPS21 all showed high specificity towards NPP, (Z,Z)-FPP, and NNPP, respectively compared to their all-trans counterparts.

Even some class II diTPSs (TPS-c) have been shown to have promiscuous activities in converting NNPP into irregular labdane structures. The substrate promiscuity of these TPSs suggests that the evolution of a prenyl transferase to afford an unusual terpene precursor may not require the co-evolution of a TPS, as the ability to convert a novel substrate may already be present in lineages where promiscuity was never selected against. Additionally, the occurrence of TPSs which natively convert cis-prenyl substrates is widespread throughout different TPS subfamilies. Examples have now been seen in the TPS e/f (*Solanum* species), TPS-b (*Eremophila lucida*), and TPS-a (*L. frutescens* and three *Eremophila* species) subfamilies, showing that evolution towards specificity for these substrates has happened independently in vastly different lineages of TPSs. Taken together, the presence of uncommon substrates may be more widespread than generally assumed, and the search for biosynthetic routes to new terpene backbones should involve a consideration of other possible precursors beyond the all-trans substrates which are typical.

The following statements are intended to describe and summarize various features of the invention according to the foregoing description provided in the specification and figures.

Statements:

An expression system comprising one or more expression cassettes, each expression cassette comprising a promoter operably linked to a nucleic acid segment encoding at least one of the following enzymes: a cis-prenyl transferase, a terpene synthase, a cytochrome P450, or a combination thereof.

The expression system of statement 1, wherein the cis-prenyl transferase, the terpene synthase, or the cytochrome P450 nucleic acid segment is from a *Leucophyllum frutescens* (Lf), *Tripterygium wilfordii* (Tw), *Euphorbia peplus* (Ep), *Coleus forskohlii* (Cf), *Ajuga reptans* (A), *Perovskia atriciplifolia* (Pa), *Nepeta mussini* (Nm), *Origanum majorana* (Om), *Hyptis suaveolens* (Hs), *Grindelia robusta* (Gr), *Leonotis leonurus* (Ll), *Marrubium vulgare* (Mv), *Vitex agnus-castus* (Vac), *Euphorbia peplus* (Ep), *Ricinus communis* (Rc), *Daphne genkwa* (Dg), or *Zea mays* (Zm) organism.

The expression system of statement 1 or 2, wherein the cis-prenyl transferase, the terpene synthase, or the cytochrome P450 enzyme is from a *Leucophyllum frutescens* (Lf).

The expression system of statement 1, 2 or 3, further comprising one or more expression cassettes, each expression cassette comprising a promoter operably linked to a nucleic acid segment encoding at least one of the following enzymes: more transcription factor, terpene synthase, cytochrome P450 reductase, 1-deoxy-D-xylulose 5-phosphate synthase (DXS), 1-deoxy-D-xylulose 5-phosphate-reducto-isomerase, cytidine 5'-diphosphate-methylerythritol (CDP-ME) synthetase (IspD), 2-C-methyl-d-erythritol 2,4-cyclodiphosphate synthase (IspF), geranylgeranyl diphosphate synthase (GGDPS), HMG-CoA synthase, HMG-CoA reductase (HMGR), mevalonic acid kinase (MVK), phosphomevalonate kinase (PMK), mevalonate-5-diphosphate decarboxylase (MPD), isopentenyl diphosphate isomerase (IDI), abietadiene synthase (ABS), farnesylpyrophosphate synthase (FPPS), ribulose bisphosphate carboxylase, squalene synthase (SOS), patchoulol synthase, or WRI1 protein.

A host cell comprising an expression system comprising one or more expression cassettes, each expression cassette comprising a promoter operably linked to a nucleic acid segment encoding at least one of the following enzymes: a cis-prenyl transferase, a terpene synthase, a cytochrome P450, or a combination thereof.

The host cell of statement 5, wherein the cis-prenyl transferase, the terpene synthase, or the cytochrome P450 nucleic acid segment is from a *Leucophyllum frutescens* (Lf), *Tripterygium wilfordii* (Tw), *Euphorbia peplus* (Ep), *Coleus forskohlii* (Cf), *Ajuga reptans* (Ar), *Perovskia atriciplifolia* (Pa), *Nepeta* mussini (Nm), *Origanum majorana* (Om), *Hyptis suaveolens* (Hs), *Grindelia robusta* (Gr), *Leonotis leonurus* (Ll), *Marrubium vulgare* (Mv), *Vitex agnus-castus* (Vac), *Euphorbia peplus* (Ep), *Ricinus communis* (Rc), *Daphne genkwa* (Dg), or *Zea mays* (Zm) organism.

The host cell of statement 5 or 6, wherein the cis-prenyl transferase, the terpene synthase, or the cytochrome P450 enzyme is from a *Leucophyllum frutescens* (Lf).

The host cell of statement 5, 6 or 7, further comprising one or more expression cassettes, each expression cassette comprising a promoter operably linked to a nucleic acid segment encoding at least one of the following enzymes: more transcription factor, terpene synthase, cytochrome P450 reductase, 1-deoxy-D-xylulose 5-phosphate synthase (DXS), 1-deoxy-D-xylulose 5-phosphate-reductoisomerase, cytidine 5'-diphosphate-methylerythritol (CDP-ME) synthetase (IspD), 2-C-methyl-d-erythritol 2,4-cyclodiphosphate synthase (IspF), geranylgeranyl diphosphate synthase (GGDPS), HMG-CoA synthase, HMG-CoA reductase (HMGR), mevalonic acid kinase (MVK), phosphomevalonate kinase (PMK), mevalonate-5-diphosphate decarboxylase (MPD), isopentenyl diphosphate isomerase (IDI), abietadiene synthase (ABS), farnesylpyrophosphate synthase (FPPS), ribulose bisphosphate carboxylase, squalene synthase (SQS), patchoulol synthase, or WRI1 protein.

A method comprising contacting terpene or terpenoid substrate with one or more of the following enzymes cis-prenyl transferase, a terpene synthase, a cytochrome P450 to thereby synthesize at least one serrulatane.

The method of statement 9, wherein the product comprises leubethanol (1).

The method of statement 9 or 10, which is performed in vitro in a cell-free mixture.

The method of statement 9, 10 or 11, which is performed within a cell that expresses at least one of the enzymes.

The method of statement 12, wherein the cell is a host cell comprising an expression system comprising one or more expression cassettes, each expression cassette comprising a promoter operably linked to a nucleic acid segment encoding at least one of the following enzymes: a cis-prenyl transferase, a terpene synthase, a cytochrome P450, or a combination thereof.

The specific methods, expression systems, and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention.

The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

One of ordinary skill in the art will recognize that the methods of the current disclosure can be achieved by administration of a composition described herein comprising at least one bronchodilator and at least one pulmonary surfactant via devices not described herein.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading can occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The term "substantially no" as used herein refers to less than about 30%, 25%, 20%, 15%, 10%, 5%, 3%, 2%, 1%, 0.5%, 0.1%, 0.05%, 0.001%, or at less than about 0.0005% or less or about 0% or 0%.

Those skilled in the art will appreciate that many modifications to the embodiments described herein are possible without departing from the spirit and scope of the present disclosure. Thus, the description is not intended and should not be construed to be limited to the examples given but should be granted the full breadth of protection afforded by the appended claims and equivalents thereto. In addition, it is possible to use some of the features of the present disclosure without the corresponding use of other features. Accordingly, the foregoing description of or illustrative embodiments is provided for the purpose of illustrating the principles of the present disclosure and not in limitation thereof and can include modification thereto and permutations thereof.

What is claimed is:

1. A host cell comprising an expression system comprising one or more expression cassettes, each expression cassette comprising a promoter operably linked to a nucleic acid segment encoding at least one of: a short chain cis-prenyl transferase having 90% identity to SEQ ID NO:1, a terpene synthase having 90% identity to SEQ ID NO:3, and a cytochrome P450 CYP71D616 having 90% identity to SEQ ID NO:5.

2. The host cell of claim 1, wherein more than one of the cis-prenyl transferase, the terpene synthase, or the cytochrome P450 are encoded, and the additional enzyme nucleic acid segment is from *Leucophyllum frutescens* (Lf), *Tripterygium wilfordii* (Tw), *Euphorbia peplus* (Ep), *Coleus forskohlii* (C), *Ajuga reptans* (Ar), *Perovskia atriciplifolia* (Pa), *Nepeta mussini* (Nm), *Origanum majorana* (Om), *Hyptis suaveolens* (Hs), *Grindelia robusta* (Gr), *Leonotis leonurus* (Ll), *Marrubium vulgare* (Mv), *Vitex agnus-castus* (Vac), *Euphorbia peplus* (Ep), *Ricinus communis* (Rc), *Daphne genkwa* (Dg), or *Zea mays* (Zm) organism.

3. The host cell of claim 1, wherein the host cell encodes more than one of cis-prenyl transferase, the terpene synthase, or the cytochrome P450 enzyme, and the enzymes are from *Leucophyllum frutescens* (L).

4. The host cell of claim 1, further comprising one or more additional expression cassettes, each additional expression cassette comprising a promoter operably linked to a nucleic acid segment encoding at least one of the following: transcription factor, terpene synthase, cytochrome P450 reductase, 1-deoxy-D-xylulose 5-phosphate synthase (DXS), 1-deoxy-D-xylulose 5-phosphate-reducto-isomerase, cytidine 5'-diphosphate-methylerythritol (CDP-ME) synthetase (1spD), 2-C-methyl-d-erythritol 2,4-cyclo-diphosphate synthase (IspF), geranylgeranyl diphosphate synthase (GGDPS), HMG-COA synthase, HMG-COA reductase (HMGR), mevalonic acid kinase (MVK), phosphomevalonate kinase (PMK), mevalonate-5-diphosphate decarboxylase (MPD), isopentenyl diphosphate isomerase (IDI), abietadiene synthase (ABS), farnesylpyrophosphate synthase (FPPS), ribulose bisphosphate carboxylase, squalene synthase (SQS), patchoulol synthase, or WRII protein.

5. The host cell of claim 1, wherein the host cell is *Nicotiana benthamiana* or *Escherichia coli*.

* * * * *

UNITED STATES PATENT AND TRADEMARK OFFICE
CERTIFICATE OF CORRECTION

PATENT NO. : 12,378,579 B2
APPLICATION NO. : 17/905749
DATED : August 5, 2025
INVENTOR(S) : Miller et al.

Page 1 of 1

It is certified that error appears in the above-identified patent and that said Letters Patent is hereby corrected as shown below:

In the Claims

<u>In Column 53, Claim 2, Line 65:</u>
DELETE: "nucleic acid segment"

Signed and Sealed this
Second Day of December, 2025

John A. Squires
*Director of the United States Patent and Trademark Office*